United States Patent [19]

Wirth et al.

[11] 4,404,408
[45] Sep. 13, 1983

[54] COMPLEXED COMPOUNDS, PROCESSES FOR THEIR MANUFACTURE AND THEIR USE

[75] Inventors: Hermann O. Wirth, Bensheim-Auerbach; Hans-Helmut Friedrich, Lautertal-2, both of Fed. Rep. of Germany

[73] Assignee: Ciba-Geigy Corporation, Ardsley, N.Y.

[21] Appl. No.: 831,309

[22] Filed: Sep. 7, 1977

[30] Foreign Application Priority Data

Sep. 8, 1976 [CH] Switzerland .............................. 11391

[51] Int. Cl.$^3$ ...................... C07C 31/18; C07C 31/22
[52] U.S. Cl. ................... 568/680; 260/455 R; 260/455 B; 568/1; 260/456 R; 260/457; 568/8; 260/920; 260/963; 568/9; 260/967; 260/462 R; 568/63; 260/463; 260/466; 568/39; 568/40; 568/41; 568/46; 568/50; 568/55; 568/57; 568/606; 568/613; 568/626; 568/671; 568/672; 568/680; 260/439 R; 260/438.1; 260/429.9; 260/429.7; 260/429 J; 260/429.5; 260/429.3; 260/438.5 R; 260/430; 260/435 R; 260/436; 260/446; 260/447; 260/431; 260/454

[58] Field of Search .................... 568/13, 1, 8, 9, 63, 568/39, 40, 41, 46, 50, 55, 57, 606, 613, 626, 671, 672, 680; 260/439 R, 438.1, 429.9, 429.7, 429 J, 429.5, 429.3, 438.5 R, 430, 435 R, 436, 446, 447, 431, 454, 455 R, 455 B, 456 R, 457, 920, 963, 967, 462 R, 463, 466

[56] References Cited

U.S. PATENT DOCUMENTS 4,089,881 5/1978 Lukehart ...................... 260/429 J X Primary Examiner—Paul F. Shaver
Attorney, Agent, or Firm—Luther A. R. Hall

[57] ABSTRACT

Metal or metalloid salts, ansolvo-acids and proton-acids can be so complexed with 1,2,3-triols, glycerol ethers or glycerol thioethers containing at least 6 C atoms in the molecule that they are in the form of compositions which are soluble in organic solvents, especially non-polar, aprotic solvents, such as hydrocarbons. These stable compositions display an outstanding anti-static action and, because of their spectrum of properties, are especially suitable for imparting anti-static characteristics to polymers, lubricants, fuels and also solvents based on hydrocarbons.

6 Claims, No Drawings

COMPLEXED COMPOUNDS, PROCESSES FOR THEIR MANUFACTURE AND THEIR USE

The present invention relates to complexed compounds of preferably inorganic salts, proton-acids or ansolvo-acids with specific 1,2,3-triols, glycerol monoethers or glycerol monothioethers as the complex-forming compounds, processes for their manufacture and their use as additives having an anti-static action in natural and synthetic polymers, lubricants and fuels based on hydrocarbons.

Glycerol monoesters, glycerol monoethers and glycerol monothioethers are known as anti-static active compounds for polymers from DT-AS No. 2,234,016 and German Offenlegungsschriften Nos. 1,930,343 and 2,500,315. Although these compounds possess excellent activities, there is a desire to modify them so that a wider range of application for other substrates also, and higher activities, can be achieved.

It is also already known to react various inorganic salt-like compounds with monofunctional or polyfunctional alcohols and these compounds are variously described as alcohol complexes.

Thus, reaction products of basic aluminium salts with organic polyhydroxy compounds are described in U.S. Pat. No. 3,420,932. In addition to various diols, glycerol is also mentioned as a triol. These products obtained by a direct reaction of the basic aluminium salts with the polyhydroxy compounds have the considerable disadvantage that they are soluble only in polar, protic solvents, such as, for example, alcohols and, on the other hand, are completely insoluble in non-polar, aprotic solvents, such as aliphatic or aromatic hydrocarbons. A possible explanation of this characteristic is that, with the reaction described, complex polymers are produced via the formation of an alcoholate, as is indicated for a similar process in German Patent Specification No. 1,468,537, column 4, lines 10-21. The products described in this patent are also readily soluble in alcohols but merely dispersible in a polar organic solvent, such as halogenated hydrocarbons.

It is described on pages 1456 to 1458 of Analytical Chemistry, Volume 41, No. 11 (1969) that barium hydroxide forms alcoholates with diglycerol and that hydroxyl groups which are still free in the diglycerol are able to form chelate bonds to the barium cation. Because of the strongly polar character of the ligand, these chelated alcoholates are also virtually insoluble in hydrocarbons.

Kim. Tekknol. Topal. Masel, 11 (1974), pages 25-28 describes the reaction of molybdenum pentachloride with $C_{12}$-$C_{14}$-1,2-diols, alcoholates being formed as the reaction products, with the elimination of hydrogen halide. Alcoholates of diols and molybdenum halides are also described in German Patent Specification No. 954,448. These alcoholates are soluble in mineral oils. A disadvantage of these compounds is that active constituents of the compound, in this case the halogen atoms, are replaced by the formation of the alcoholate.

A process for the isomerisation of dichlorobutene, which is carried out in the presence of a catalyst mixture consisting of copper naphthenate and 1,2-diols, for example β-methoxypropane-1,2-diol, is known from DT-OS No. 2,159,012. However, nowhere is it mentioned that this mixture of catalysts is a complex or that a complex is formed during the isomerisation. Moreover, no favourable solubility properties would be expected from such a complex.

It is described in J. inorg. nucl. Chem., 1972, Vol. 34, pages 357-359 that lanthanum perchlorates are able to form complexes in aqueous solution with polyols, for example glycerol. These complexes also are not soluble in non-polar, aprotic solvents.

Reaction products obtained from, for example, lead oxide, fatty acids or higher carboxylic acids and alkoxyalcohols, such as 2-ethoxy-ethanol, or polyols, such as sorbitol, are designated oil-soluble metal complexes in French Patent Specification No. 2,264,082. The solubility of these products is based, in the case of these reaction products, on the acid constituent, which has a high carbon content, and on the alkoxy-alkanol or polyol. Thus, this does not deal with the problem of converting salts by means of only one complex-forming reagent into products which are then soluble in non-polar, aprotic solvents. The low stability to heat of the products described, which results from the low complexing power of the alcohols proposed, should be mentioned as a disadvantage of these products.

Nickel complexes which are obtained from nickel salts of hydroxy- and alkyl-substituted phenyl-carboxylic acids with alcohols or polyols, and which have a good stability to heat and are used as light stabilisers in polymers, are described in DT-OS No. 2,330,906. Here also, this does not deal with the problem of converting salts by means of a specific complex-forming reagent into products which, for example, are soluble in hydrocarbons.

In addition, it may also be mentioned that the category of metals salts complexed with crown ethers can also comprise compounds soluble in non-polar, aprotic solvents. Disadvantages of these complexes are the specific complexing ability of the crown ethers for specific cations only and the involved, uneconomical synthesis of the crown ethers themselves.

One object of the present invention is to provide a complexed compound, which is stable to heat, of a metal salt or metalloid salt or of a proton-acid or ansolvo-acid, which compound is also soluble in non-polar aprotic solvents and is an effective anti-static additive in this solvent, in lubricants or in polymers. A further object of the present invention is to indicate a general process for the manufacture of this complexed compound.

The present invention relates to complexed compounds, which correspond to the composition I, of a metal or metalloid salt, ansolvo-acids or proton-acids, or to mixtures thereof,

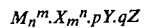  (I)

$$M_n{}^m.X_m{}^n.pY.qZ$$

in which M represents a m-valent cation of a metal or metalloid, a metal-oxy or metal-dioxy cation or a proton, X denotes a n-valent anion of a n-basic inorganic proton-acid or of a n-basic organic acid of the group comprising the aliphatic and cycloaliphatic carboxylic acids which have up to 8 C atoms and can be substituted by halogen and/or hydroxyl groups, the aromatic mono-, di- and tri-carboxylic acids, which can be substituted by hydroxyl, halogen and/or nitro groups, the organic oxy-acids of phosphorus and sulphur and the organic thio-acids of phosphorus and of the group comprising the mercaptans, the inorganic or organic acid having a $pK_a$ value of at most 15.8, and of at most 11 if M is a proton, Y is water or a neutral organic molecule, which can be bonded by a coordinate bond to the cation or to the anion, Z denotes a complex-forming compound from the group comprising the 1,2,3-triols or glycerol monoethers or glycerol thioethers, with at least 6 C atoms, p represents 0 or a value between 0 and 2, q is a value from 1 to 32, m is an integer from 1 to 6, and is the number 1 if M is a proton, and n denotes an integer from 1 to 4.

The composition I comprises only monomeric salts; in the partial formula $M_n{}^m X_m{}^n$, therefore, the subscripts n and m are always 1 if the superscripts m and n are identical numbers. X in the monomeric salts can, however, denote a polymeric anion.

The m-valent cation is preferably derived from a metal of groups 1a to 8a and 1b to 5b of the periodic table of the elements, the lanthanides, uranium, plutonium or the metalloids boron, silicon, germanium and antimony. The valency m of the cation results from the position of the elements in the periodic table. In the present application, the valency is understood as the number m of electrons which a metal is able to release with the formation of a metal ion with a charge of m. As is generally known, an element can form different stable valency states, for example tin can be in the divalent or tetravalent form, chromium can be in the divalent or trivalent form or copper can be in the monovalent or divalent form. A valency of 6 is realised, for example, in tungsten hexafluoride. The valency m is preferably 1 to 5.

The cation is particularly preferentially derived from the elements Li, Na, K, Be, Mg, Ca, Sr, Ba, Al, Sc, La, Ce, Eu, Ti, Zr, Hf, Th, V, Nb, Ta, Cr, Mo, W, U, Mn, Fe, Co, Ni, Rh, Pd, Os, Ir, Pt, Cu, Ag, Au, Zn, Cd, Hg, Sn, Pb and Bi and the metalloids B, Si, Ge and Sb.

In particular the cation is derived from the metals Li, Na, K, Mg, Ca, Sr, Ba, Al, Ti, Zr, V, Cr, Mo, W, Mn, Fe, Co, Ni, Cu, Ag, Au, Zn, Cd, Sn, Pb and Bi and the metalloids B, Si and Sb.

Some metals can also form metal-oxo cations which contain one or two oxygen atoms. Amongst these, titanyl, vanadyl, zirconyl and uranyl are preferred. The tetravalent cation tungstenyl and the monovalent cations antimonyl and bismuthyl may also be mentioned.

The inorganic acid and the organic acids defined above, from which the anion is derived, preferably have a pKa value of at most 10 and especially of at most 4 and in the case of the strongest acids this value is down to about −10. As is generally known, the pKa value, which is a measure of the acid strength, for protolytes in aqueous systems is defined as the negative common logarithm of the equilibrium constant of the protolysis reaction. The same definition also applies to the $pK_b$ values, which are a measure of the base strength. It has been found that those chelated compounds, according to the invention, of the formula I which are derived from strong acids are particularly stable. The upper limit of the $pK_a$ value of 15.8 also includes water as a weak acid.

X is the anion of a n-basic inorganic or organic proton-acid of the type defined above. This definition also includes proton-acids which do not exist in the free form but exist only in the form of their salts, for example the ammonium salts. The basicity n gives the number of negative charges formed on the anion by the elimination of n protons. In addition to the anions of monobasic acids such as hydrochloric acid, anions of tetrabasic acids are also known, such as, for example, silicate or titanate, and n therefore denotes integers from 1 to 4. X also comprises polymeric anions, for example those of the silicates, titanates, phosphates, arsenates, zirconates, vanadates, borates, molybdates, tungstates and antimonates.

The anion X is preferably derived from inorganic proton-acids from the group comprising the hydrogen halide acids and hydrogen pseudohalide acids and hydroselenic acid, the inorganic oxy-acids or thio-acids and the inorganic complex acids.

Amongst the hydrogen halide acids and hydrogen pseudohalide acids, those which may be mentioned are: HF, HCl, HBr, HI, HCN, HCNO, HCNS and $HN_3$.

The inorganic oxy-acids are preferably derived from the elements C, N, P, As, S, Se, Cl, Br and iodine or from the amphoteric elements and the metalloids. The inorganic thio-acid is preferably $H_2S$ or is derived from the elements C, V, Mo, W, Sn, P, As, Sb and S.

Examples which may be mentioned of anions of the oxyacids of the said elements are: carbonate, bicarbonate, nitrite, nitrate, hypophosphite, phosphite, orthophosphate, polyphosphates such as diphosphates, metaphosphates such as metaphosphate, trimetaphosphate or tetrametaphosphate, fluorophosphate, arsenite, arsenate, sulphite, sulphate, peroxomonosulphate, peroxodisulphate, thiosulphate, dithionite, dithionate, pyrosulphite, pyrosulphate, polythionate, fluorosulphonate selenite, selenate, tellurite, tellurate, hypochlorite, chlorite, chlorate, perchlorate, bromite, bromate, iodate and periodate.

Anions of thio-acids which may be mentioned are, in addition to sulphide: polysulphides such as disulphide, thiocarbonate, thionocarbonate, thiothionocarbonate, dithionocarbonate, trithiocarbonate, thiovanadate, thiomolybdate, thiotungstate, thiostannate, thioantimonate, thioarsenate, thioarsenite, thioantimonite, trithionophosphate, tetrathiophosphate and trithiophosphite.

Anions of oxy-acids of the amphoteric elements and of the metalloids which may be mentioned are: borate, metaborate, silicate, metasilicate, germanate, antimonite, antimonate, aluminate, titanate, zirconate, vanadate, chromate, dichromate, molybdate, tungstate, manganate, permanganate, stannite and stannate.

Anions of inorganic complex acids are understood as those which are built up from a central metal or metalloid atom and complex-forming acido-ligands. Suitable metals and metalloids are, for example, B, Si, Ge, As, Sb, Al, Ti, Zr, V, Nb, Ta, Cr, Mo, W, Mn, Zn, Cd, Fe, Co, Ni, Ru, Rh, Pd, Os, Ir, Pt, Cu, Ag, Au, Sn, Pb and Bi. Suitable acido-ligands are, for example, the halides, especially fluoride and chloride, the pseudohalides, especially cyanide and thiocyanate, the CO group and oxalate. These complex anions belong, in the main, to the $[MX_4]^n$, $[MX_5]^n$ and $[MX_6]^n$ types, in which M is the metal ion or metalloid ion, the X are the acido-ligands and n is the basicity (negative charge), which result from the valency of the metal or metalloid and the charge of the acido-ligands. It should also be mentioned that, amongst the many complex anions, polynuclear complex anions are also known. Examples are: tetrafluoborate, hexafluorosilicate, hexafluoroarsenate, hexafluoroantimonate, pentafluoroantimonate-III, hexafluorophosphate, tetrafluoroaluminate, hexafluoroaluminate, hexafluorotitanate, hexafluoromolybdate or hexafluorotungstate, hexafluorochromate-III, hexafluoroferrate, hexafluorocobaltate, hexafluoroplatinate, tetrafluorozincate, hexafluorostannate, hexafluoroplumbate, hexafluoromanganate, hexafluororhodate, hexachloroiridate, hexafluorotantalate or hexafluoroniobate, tetrachloroaluminate, hexachlorotitanate, hexachlorovanadate, tetrachlorovanadate, hexachlorochromate, hexachloromanganate, hexachloromolybdate and hexachlorotungstate, hexachloroferrate, tetrachloronickelate, hexaiodotechnate, hexachlororhenate, hexachlororuthenate, hexachloroosmiate, hexachlorostannate, hexachloroplumbate, hexachloroantimonate, hexachlorobismuthate, tetrabromocadmiate, tetracyanozincate, tetra-chloro-,-bromo- or-iodo-mercurate, tetracyanomercurate, tetrathiocyanatomercurate, hexacyanovanadate, trioxalatovanadate, hexacyanochromate, trioxalatochromate, pentacyanonitrosochromate, hexacyanomanganate, hexathiocyanatomanganate, trioxalatomanganate, hexacyanoferrate, tetracyanocobaltate, tetracyanonickelate, tetracyanocuprate, tetraoxalatozirconate, hexathiocyanatomolybdate, octacyanomolybdate, octacyanotungstate, octacyanorhenate, hexacyanoplatinate, hexacyanoosmiate, tetracyanopalladate, pentacarbonylmanganate, tetracarbonylferrate and tetracarbonylcolbaltate.

Some of the complex acids are known in the free form and others are known only in the form of their salts, for example the ammonium salts.

X can also be the anion of a n-basic aliphatic or cycloaliphatic carboxylic acid which has at most 8 C atoms, preferably 1 to 4 C atoms, and can be substituted by halogen or hydroxyl. The carboxylic acid is preferably substituted in the α-position, especially by fluorine, chorine or bromine, and the carboxylic acid is preferably monobasic or dibasic. Examples are: formate acetate, propionate, butyrate, oxalate, malonate, succinate, fumarate, maleate, dithiodipropionate, hydroxyacetate, mono-, di- and tri-fluoroacetate, mono-, di- and tri-chloroacetate, mono-, di- and tri-bromoacetate, α-chloropropionate, α-chloro- or α-bromo-malonate and 1,2-dichloro- or -dibromo-succinate.

X can also be the anion of an aromatic carboxylic acid which has, preferably, up to at most 12 C atoms, is preferably chosen from the group comprising the monobasic to tribasic phenylic and naphthylic acids and can be substituted by halogen, especially fluorine, chlorine or bromine, or by nitro groups. Examples are: benzoate, isophthalate, terephthalate, 2-naphthenate, 2,6-dinaphthenate, chlorobenzoate and nitrobenzoate.

X can also be the anion of an organic oxy-acid of phosphorus and sulphur and of an organic thio-acid of phosphorus. These acids are preferably the phosphonic, phosphinic, thiophosphonic, thiophosphinic, sulphonic and sulphinic acids. The acids of phosphorus can be represented by the following general formula

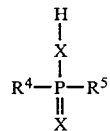

in which $R^4$ denotes a hydrocarbon radical of aliphatic or aromatic character which has, preferably, up to 18, and especially up to 8, C atoms and can be substituted by halogen, especially fluorine and chlorine, the X independently represents oxygen or sulphur and $R^5$ is the group —XH or a hydrogen or independently has the same meaning as $R^4$.

The oxy-acids of sulphur can be represented by the following formula,

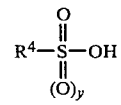

in which $R^4$ has the meaning indicated above and y is 0 or 1. $R^4$ can be linear or branched alkyl, cycloalkyl, aryl or aralkyl, which can be substituted, in particular by fluorine or chlorine and alkyl with 1 to 6 C atoms. Cycloalkyl is preferably cyclohexyl and aryl and aralkyl are preferably derived from phenyl and naphthyl.

Examples are: methyl, ethyl, propyl, isobutyl, octyl, octadecyl, phenyl, naphthyl, p-methylphenyl, butylphenyl, dibutylphenyl, hexylphenyl, chloromethyl, chloroethyl, chlorophenyl, fluoromethyl and trifluoromethyl.

X can also be the anion of a mercaptan, which preferably contains up to 18 and especially contains up to 12 C atoms. The mercaptan preferably corresponds to the formula

in which $R^6$ is linear or branched alkyl, which is optionally interrupted by oxygen, or hydroxyalkyl, alkoxycarbonylalkyl or phenyl which is optionally substituted by $C_1$–$C_{12}$ alkyl. Examples are: methyl, ethyl, propyl, hexyl, octyl, decyl, dodecyl, octadecyl, β-hydroxyethyl, β-hydroxypropyl, alkoxycarbonylmethyl and β-alkoxycarbonylethyl, such as, for example, i-octoxycarbonylmethyl or i-octoxycarbonylethyl, thiophenol and nonylthiophenol.

The anion X can also be derived from dibasic to tetrabasic oxy-acids which are partially esterified, preferably by $C_1$–$C_{12}$-alkanols or phenols.

Mixtures which contain a compound, according to the invention, of the composition I, in which X represents an anion of the type defined above, and also one or more compounds of the composition I in which X represents an alcoholate anion are also included within the scope of the present invention. The alcoholate anion can be derived from alkanols or phenols which have, preferably, 1 to 8 C atoms and in this case X then at the same time also represents an alcoholate anion which is derived from a complexing compound of the formula Z. Preferably, X alone represents the last-mentioned alcoholate anion. These mixtures are obtained when a metal alcoholate or metalloid alcoholate obtained from the abovementioned alcohols and a metal or metalloid which is at least divalent is reacted with a less than equivalent amount of an anhydrous compound of the formula $H_nX^n$ or an ammonium salt of the formula $A_nX^n$. Statistical mixtures, the composition of which is essentially determined by the extent to which the amount of the anhydrous compound or ammonium salt used falls below the equivalent amount, are obtained from this reaction. In some cases, this mixture can also contain starting material which has not yet reacted. If X is intended to denote an alkanolate or phenolate anion, a reaction product of a metal alcoholate or phenolate or a metalloid alcoholate or phenolate is employed with a less than equivalent amount of a complexing compound of the formula Z.

Some preferred anions are hydroxyl, fluoride, chloride, bromide, iodide, cyanide, cyanate, thiocyanate, azide, perchlorate, bromate, iodate, periodate, permanganate, sulphide, hydrogen sulphide, hydrogen difluoride, nitrite, nitrate, sulphite, sulphate, thiosulphate, hydrogen sulphate, fluorosulphate, hydrogen sulphite, phosphate, hydrogen phosphate, phosphite, hypophosphite, metaphosphate, polyphosphate, monofluorophosphate, carbonate, bicarbonate, thiocarbonate, thionocarbonate, dithiocarbonate, thionothiocarbonate, trithionocarbonate, carbamate, xanthate, trithionophosphate, tetrathiophosphate, trithiophosphite, silicate, metasilicate, titanate, borate, metaborate, molybdate, vanadate, aluminate, chromate, dichromate, selenate, tungstate, arsenite, arsenate, antimonate, stannate, thioarsenite, thioarsenate, thioantimonate, thiostannate, thiomolybdate, thiotungstate, tetrafluoborate, hexafluorosilicate, hexafluorotitanate, hexafluoroaluminate, hexachlorostannate, hexachloroferrate, hexacyanoferrate, octacyanomolybdate, hexafluoroantimonate, hexacyanochromate, tetracyanonickelate, trioxalatomanganate, methylphosphonate, methylphosphinate, phenylphosphonate, tosylate, phenylsulphonate, methylsulphinate, formate, acetate, propionate, benzoate, terephthalate, trifluoroacetate, trichloroacetate, chlorobenzoate, trifluoromethylsulphonate, oxalate, malonate, maleate, fumarate, hydroxyacetate, naphthylsulphonate, dithiodipropionate, methylmercaptide, phenylmercaptide, octoxycarbonylmethylmercaptide and β-hydroxyethylmercaptide.

Preferred anions in the compound, according to the invention, of the composition I are especially those which are derived from inorganic acids which, in particular, have a $pK_a$ value of at most 7.5 and the anions of the organic acids which have a $pK_a$ value of at most 4. If M denotes a proton, the $pK_a$ value is preferably at most 9.5 and especially at most 4.

$M_n{}^m \cdot X_m{}^n$ can also denote ansolvo-acids.

Examples which may be mentioned are: $BF_3$, $BCl_3$, $AlF_3$, $AlCl_3$, $SiCl_4$, $TiCl_4$, $SnCl_2$, $SnCl_4$, $SbF_5$, boron trialcoholates and alkyl-tin oxides. Further examples are well known to those skilled in the art.

M in the composition I can also denote a proton. These are then to be understood as the inorganic and organic oxygen-containing and oxygen-free protonacids, the anions of which have been defined above. The oxygen-contain proton-acids are preferred.

When Y denotes water, this can, in the compounds of the composition I, be bonded by a coordinate bond to the cation or the anion or can be in the form of water of crystallisation. In some cases it is possible that the water cannot be removed completely. The compounds preferably contain no water or only very little water.

Y in the composition I can also be an organic molecule which can be bonded by a coordinate bond, preferably ethanol, diethyl ether, tetrahydrofurane, dimethylformamide, dimethylsulphone or tetramethylenesulphone. These compounds can remain in small amounts in the chelated compounds of the composition I if the manufacture is effected in the corresponding solvent.

In general, however, water and the said organic molecules of the formula Y can be removed virtually completely, so that p preferably is a value of 0 to 1 and especially 0.

Z in the compounds, according to the invention, of the composition I, as a complex-forming compound, preferably contains branched, especially long-chain branched, radicals with, preferably, 6–14 C atoms. Long-chain branching is preferably understood as a $C_2$-$C_8$-alkyl side chain. Z preferably has a total of 8 to 30 and especially 8 to 21 C atoms.

The 1,2,3-triol which has, preferably, 8 to 24, and especially 8 to 18, C atoms, corresponds, in particular, to the general formula II

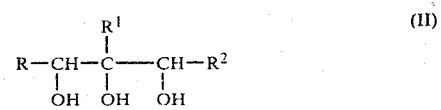 (II)

in which R represents a hydrocarbon radical of aliphatic or aromatic character which has, preferably, 3 to 20, and especially 5 to 15, C atoms, and $R^1$ and $R^2$ independently have the same meaning as R or, in particular, independently of one another, are a hydrogen atom. Preferably, R, $R^1$ and $R^2$ are linear and especially branched alkyl with, in particular, 5 to 15 C atoms. The 1,2,3-triols are known compounds and are manufactured from α,β-unsaturated alcohols by glycolisation reactions, as is described, for example, in German Patent Specification No. 1,149,700.

A sub-group of the 1,2,3-triols comprises the ethers and thioethers which are obtainable by reaction of mono-1,2-epoxy-3,4-dihydroxybutane, -2-methylbutane or -2,3-dimethylbutane with mercaptans or alcohols of the formula $R^3LH$, in which $R^3$ and L have the meaning given below. The 1,2-3,4-diepoxides of butane, 2-methylbutane and 2,3-dimethylbutane can also be employed as starting materials. The starting materials are readily accessible by the epoxidation of butadiene, isoprene or 2,3-dimethylbutadiene.

A further sub-group comprises partially etherified sugar alcohols and sugars which contain a 1,2,3-triol group and optionally contain further hydroxyl groups.

As a complex-forming compound, Z is also a monoglycerol ether or thioether with, preferably, a total of 8 to 30, and especially 8 to 24, C atoms. These ethers and thioethers contain the structural element

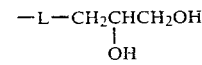

in which L denotes O or S. These esters, ethers and thioethers preferably correspond to the general formula III

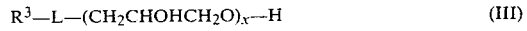 (III)

in which x denotes a value from 0.5 to 8, L denotes S or, preferably, O and $R^3$ denotes a hydrocarbon radical of aliphatic or aromatic character which has, preferably, 3 to 24, and especially 5 to 18, C atoms and is optionally interrupted by oxygen or sulphur atoms.

$R^3$ is preferably linear or, especially, branched, alkyl which is optionally interrupted by O or S atoms, or cycloalkyl, aryl or aralkyl which are optionally substituted by alkyl groups with, preferably, 1 to 12 C atoms.

Branched alkyl radicals which are derived from industrial alcohols, such as, for example, Guerbet alcohols and Alfols (manufacturer Condea), Dobanols (manufacturer Shell) and Oxanols (manufacturer Ruhr-Chemie), are particularly suitable.

The cycloalkyl preferably contains 5 to 8 ring carbon atoms and is especially cyclohexyl. Aryl preferably represents phenyl and aralkyl preferably represents benzyl, and these are substituted by 1 to 2 alkyl groups with, preferably, 1 to 12 C atoms. In formula III $R^3$ is particularly preferentially linear, and especially branched, alkyl with 5 to 18 C atoms.

Alkyl interrupted by S or O are, in particular, radicals which are derived from reaction products of alcohols or mercaptans with ethylene oxide and/or propylene oxide. The radicals preferably do not contain more than 10 alkylene oxide units. These radicals can be represented by the general formula $$R^3—L—(CHR'CH_2O)_N$$

in which $R^3$ and L independently of one another have the same meaning as above, R' represents hydrogen or methyl and n is a value from 1 to 15 and preferably 1 to 10.

The glycerol monoethers and monothioethers are known compounds and are described, for example, in DT-AS No. 2,234,016, DT-OS No. 2,500,315 and DT-OS No. 1,930,343, and the possible methods of manufacture for these compounds are also indicated in these publications. The oxidation products of glycerol monothioethers are also suitable. These sulphines or sulphones are excellent even for specially stable compositions, according to the invention, of the formula I.

The aliphatic glycerol monoethers are obtained, for example, most simply by reaction of alcohols with glycidol in the presence of a catalyst:

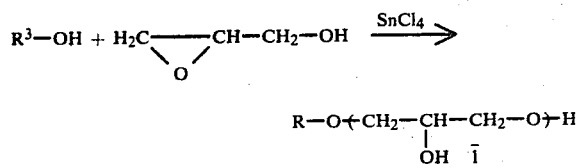

The reaction product is a statistical mixture which can even be used per se for the compounds according to the invention. Isolation of the monoether containing molecules of a single type:

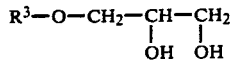

can be effected easily by distillation. At a higher distillation temperature it is also possible to separate off suitable higher glycidol adducts, such as, for example:

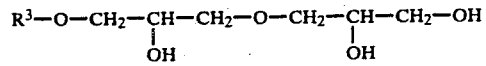

Higher glycidol adducts can also be separated off with the aid of the molecular distillation technique.

In formula III, x can therefore assume any desired value from 0.5 to 8, depending on the ratio in which the reactants are employed. However, those compounds of the formula III in which x is a value from 1 to 4 and especially 1 to 2 have proved particularly advantageous.

It is not necessary to use the chelate-forming compounds of the formula Z in the form of substances containing molecules of a single type. It is also possible successfully to employ the statistical mixtures direct for the chelation. In some cases, however, it can be advantageous if at least the starting alcohol is previously removed by distillation and if compounds of the formula III having a narrow distribution are employed.

Another route to the alkyl glycerol monoethers leads via the addition products of epichlorohydrin with alcohols, such as, for example:

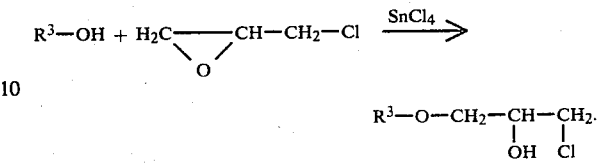

This addition reaction proceeds substantially with the formation of a single product, that is to say only a very narrow distribution arises in this case.

Saponification with, for example, sodium hydroxide solution leads to the desired glycerol ethers in this case also.

Aromatic glycerol monoethers are also readily accessible via an addition reaction wih glycidol. In this case, however, anionic catalysts, such as, for example, sodium hydride, can advantageously be employed. Under these conditions a relatively homogeneous end product is formed.

Under conditions similar to those in the case of the phenols, glycerol monothioethers can be obtained via an addition reaction of glycidol with mercaptans. In this case also relatively homogeneous reaction products are obtained. The aromatic glycerol monoethers and aromatic and aliphatic thioethers are also accessible via an addition reaction with epichlorohydrin.

The glycerol monoethers are particularly preferred as the complexing compound of the formula Z in the compounds, according to the invention, of the composition I.

Some preferred examples are: glycerol ethers of the formula

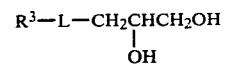

in which $R^3$-L denotes: n-pentyloxy, n-hexyloxy, n-octyloxy, i-octyloxy, i-tridecyloxy, n-hexylthio, n-octylthio, i-octylthio, tert.-dodecylthio, n-nonylphenoxy, n-octadecyloxy and also

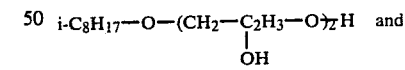

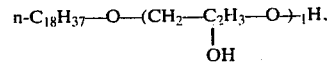

the latter representing statistical mixtures.

The value of q indicates the number of complex-forming compounds of the formula Z in the composition I and q is preferably 1 to 20, especially 1 to 16 and very particularly 1 to 8. In some of the compounds according to the invention, for example those of Li, B or Zn and others, a very good solubility, as desired, is already found when only one molecule of the complex-forming compound of the formula Z is present and this gives a lower limit of 1 for q.

It has also been found that, in compounds of the composition I which contain a relatively low-molecular compound of the formula Z, the solubility can be improved by increasing the number q of the complex-forming compound of the formula Z. Conversely, in the case of higher-molecular compounds of the formula Z, a relatively low number q suffices to achieve a good solubility.

If the compounds, according to the invention, of the composition I contain high proportions of complexing compounds of the formula Z, that is to say if q in the composition I is greater than about 16, there is a possibility that, in fact, only a portion is bonded directly to the salt, preferably to the cation.

In these cases, the compounds would then be highly concentrated solutions of the compounds according to the invention in the complexing compounds of the formula Z; these solutions also display the desired solubility properties and are also included under the present invention. Of course, it is also possible to employ mixtures of complexing compounds of the formula Z in the manufactured and the solubility can be influenced by this means.

If M denotes a proton, q is preferably 1 to 6 and especially 1 to 3. In this case, the composition I particularly preferentially contains one compound of the formula Z per proton.

Compounds, according to the invention, of the composition I can be manufactured by processes identical or analogous to those described in DT-OS No. 2,330,906. It has been found that those compounds, according to the invention, of the composition I which are derived from inorganic metal or metalloid salts, ansolvo-acids or proton-acids which are soluble in water or organic solvents can be manufactured by this process. The solubility of inorganic salts in organic solvents is described, for example, in J. Jander and Ch. Lafrenz, Wasserähnliche Lösungsmittel (Water-like Solvents), Verlag Chemie (1968).

A further subject of the present invention is, thus, a process for the manufacture of complexed compounds, of metal salts, metalloid salts, ansolvo-acids or proton-acids, of the composition I, which are derived from metal or metalloid salts, ansolvo-acids or proton-acids which are soluble in water or organic solvents, wherein the soluble metal salts or their hydrates (aquocomplexes), ansolvo-acids or proton-acids are reacted direct, in aqueous solution or as a solution in an organic solvent, with q mols per mol of metal salt or acid of a complexing compound of the formula Z and, optionally, the water or the solvent is then removed from the reaction mixture.

The process, for which various embodiments exist, is preferably carried out at temperatures of up to 150° C. and especially at 30° C. to 120° C.

In one embodiment the anhydrous metal or metalloid salts, ansolvo-acids or proton-acids are reacted direct with the complexing compounds of the formula Z. The reaction is accelerated by warming. In the case of crystalline compounds of the formula Z, a reaction temperature which is above the melting point of these compounds is appropriately chosen. The reaction has ended after the salt employed has dissolved. Any insoluble constituents can then be filtered off. Examples of anhydrous salts which may be mentioned are: $MgCl_2$, $CaCl_2$, $ZnCl_2$, $SnCl_2$, $SnBr_2$, $MnCl_2$ and $CuCl_2$. Gaseous acids such as HCl or HBr can be passed into the compounds of the formula Z, which have been initially introduced. In the case of the reaction with ansolvo-acids it is appropriate to use temperatures which are not too high, in order to suppress the replacement of the anions by alcoholate bonds.

In another embodiment metal or metalloid salts or acids containing water of crystallisation are employed and reacted with the complex-forming compounds of the formula Z.

In this case, the water of crystallisation can be removed by warming, if appropriate in vacuo, or can be driven out by azeotropic distillation with an organic solvent, such as hydrocarbons, for example hexane, heptane, petroleum ethers and also benzene, toluene, xylene or chloroform.

In general, the salt passes into solution at the rate at which the water of crystallisation is displaced. However, it has also been observed that, under certain preconditions, the salt dissolves without removal of the water of crystallisation, no demixing phenomena arising and the desired solubility again being obtained. $MgBr_2.6H_2O$ may be mentioned as an example. After the reaction, insoluble constituents can be removed by filtration and the compound according to the invention can be isolated by distilling off the solvent. Examples which may be mentioned of salts containing water of crystallisation are the hydrates of $NiCl_2$, $Ni(CH_3COO)_2$, $FeCl_2$, $AlCl_3$, $CuCl_2$, $CoCl_2$, $CaCl_2$, $MgCl_2$, $MnCl_2$, $ZnCl_2$, $CdCl_2$, $CrCl_3$, $Mg(CH_3COO)_2$, $Cu(CH_3COO)_2$ and $Co(HCOO)_2$.

When salts which, in particular, are strong Lewis acids (ansolvo-acids) are used, discolorations in the reaction product are frequently observed with this manufacturing process. It has been found, and this is a further embodiment of the process, that these discolorations can be avoided if anhydrous etheral or alcoholic solutions of the Lewis acids are used as the starting material and, after the addition of the complex-forming compound of the formula Z, the mixture is warmed to bring about the reaction and the ether or alcohol is then removed by distillation, if appropriate in vacuo. When etheral solutions are used it is also possible, prior to the addition of the compound of the formula Z, to remove the ether to such an extent that the ether adducts of the Lewis acids remain and these are employed as the starting materials. Ethers and alcohols which can be used are, in particular, low-molecular ethers and alcohols which can easily be removed by distillation, for example diethyl ether, tetrahydrofurane, methanol and ethanol. Examples of Lewis acids which may be mentioned are: $AlCl_3$, $FeCl_3$, $SnCl_4$, $MoCl_5$, $SbCl_5$, $SbF_5$, $BF_3$ and $SbF_3$.

In a further embodiment of the process, the compounds according to the invention are obtained by dissolving the anhydrous salts or acids, or the salts or acids containing water of crystallisation, in a suitable organic solvent and then adding a complex-forming compound and effecting the reaction. After removal of the solvent, the desired product is then obtained. In this process, the water of crysallisation is generally removed with the solvent. The solvents preferably used are those which are also able to dissolve the compound of the formula Z. Examples which may be mentioned are ethers, such as diethyl ether and tetrahydrofurane, alcohols, such as methanol and ethanol, and chloroform, dimethylformamide, dimethylsulphoxide or acetonitrile, and salts which may be mentioned are KI, NaBr, $AgNO_3$, $CuSO_4.5H_2O$, $Na_2S_2O_3.5H_2O$ and $Cd(CH_3COO)_2.2H_2O$.

In a particular embodiment of the process, in order to manufacture complexed compounds of the composition I in which X represents hydroxyl, a metal hydroxide or oxide, or a hydrate thereof, is reacted with q mols, per mol of hydroxide or oxide, of a complex-forming compound of the formula Z and water is then driven off in an amount such that the number of hydroxyl groups which corresponds to the valency of the metal cation remains. When metal oxides are used, it is probable that alcoholates are first formed, with the elimination of water, and are hydrolysed again by the water of reaction.

The metal oxides and hydroxides preferably employed here are those which, in aqueous solution, have $pK_b$ values of at most 9 and preferably of at most 4.5, negative values indicating very strong bases. Examples which may be mentioned are the metal oxides and hydroxides of the alkali metals and alkaline earth metals and of monovalent thallium and silver.

The processes using the proton-acids are no different in principle. Thus, the proton-acids to be complexed can be introduced directly into the complex-forming agent of the formula Z, optionally in the presence of a solvent, such as a hydrocarbon. Appropriately, the reaction mixture is cooled at this stage, and during the further reaction until a clear solution is obtained, in order not to exceed temperatures of up to 50° C. When dilute aqueous proton-acids are used, the water is advantageously removed in the presence of a complex-forming agent of the formula Z by azeotropic distillation and it is also possible to use solvents.

The complexed compounds, according to the invention, of the composition I can, surprisingly, also be manufactured via a new two-stage process in which basic or non-basic metal alcoholates or metalloid alcoholates, or esters of oxy-acids, are used as the starting materials and, in a second reaction stage, the anion is introduced. With this general process, even metal salts or metalloid salts or proton-oxy-acids which are insoluble in water and organic solvents are, surprisingly, converted into the soluble compounds according to the invention. The reaction is simple, proceeds, surprisingly, in virtually quantitative yields and has the considerable advantage that virtually all of the metal salts of acids which have a certain minimum strength can be manufactured in the form according to the invention.

A further subject of the present invention is, thus, a process for the manufacture of complexed compounds, from a metal or metalloid salt or proton-oxy acids, which correspond to the general composition I, or mixtures thereof, wherein a basic or non-basic metal alcoholate or metal oxy-alcoholate or a non-basic metalloid alcoholate or an acid ester with q mols of a complex-forming compound of the formula Z, or a compound of the composition I, in which X represents hydroxyl, is first manufactured and (a) these basic or non-basic alcoholates or compounds of the composition I, in which X denotes hydroxyl, are then reacted in the stoichiometric amount with an anhydrous compound of the formula $H_nX^n$ in which n and X have the meaning indicated above, which, in aqueous solution forms an acid which has a $pK_a$ value of at most 15.8 and if M denotes a proton has a $pK_a$ value of at most 11, or with an ammonium salt $A_nX^n$, in which A denotes an ammonium cation and n and X have the meaning indicated above, with removal of the water, ammonia or amine, or (b) the basic alcoholates or a compound of the composition I, in which X represents hydroxyl, are then reacted with a stoichiometric amount of an acid anhydride, an acid halide or an acid ester of the acids defined for the compounds of the composition I, with removal of the alcohol if an acid ester is used, or (c) in order to manufacture the compounds in which M denotes a proton, the esters of a proton-oxy-acid with a complex-forming compound of the formula Z or esters with aliphatic alcohols are reacted in the presence of q mols of a complex-forming compound of the formula Z with stoichiometric amounts of water and, when aliphatic acid esters are used, the alcohol formed is removed.

In the compounds $H_nX^n$ and $A_nX^n$ n preferably represents an integer from 1 to 3 and the $pK_a$ value of the acid is at most 7 and in particular at most 4. By way of explanation it should be mentioned that the $pK_a$ value of 15.8 just includes water as the weakest acid.

The reaction can be carried out in the presence of a solvent or without a solvent. Suitable solvents are, in particular, readily volatile ethers, such as diethyl ether, but preferably hydrocarbons, such as pentane, hexane, benzene, toluene and xylene, which can be removed again easily from the reaction mixture by distillation, if appropriate in vacuo, in order to manufacture the pure complexed compounds according to the invention. Any insoluble constituents can be filtered off before the distillation.

The process is generally carried out at ambient temperatures (about 20° C.) up to temperatures of 150° C. and preferably at 50° C. In general, a strongly positive evolution of heat is observed when the reactants (anhydrous proton-acid, acid anhydride, acid ester and acid halide) are added. In some cases it can, therefore, be appropriate to cool the reaction mixture. Warming may be necessary in order to remove the solvent used.

The metal alcoholates, metalloid alcoholates and metal oxy-alcoholates which are obtained from the complex-forming compounds of the formula Z and are used as starting materials for the process according to the invention are manufactured by various known processes:

(a) In the simplest case a metal oxide or metal hydroxide, or the hydrates thereof, are reacted with the compounds of the formula Z and, in order to manufacture the pure alcoholates, the water of reaction which has formed is removed, for example by azeotropic distillation. In order to form the basic alcoholates, only part of the water of reaction is removed.

This process is especially suitable for strong metal bases, for example those of the alkali metals and alkaline earth metals, such as NaOH, KOH, LiOH, RbOH, $Sr(OH)_2$, $Ca(OH)_2$, SrO, CaO, BaO and $Ba(OH)_2.8H_2O$.

(b) The reaction of alkali metal alcoholates or alkaline earth metal alcoholates, especially the Li, Na and K alcoholates, of the compounds of the formula Z with metal halides, metalloid halides and metal oxy-halides also leads to the corresponding alcoholates with the formation of an alkali metal halide or alkaline earth metal halide.

(c) The reaction of metal halides, for example the chlorides and bromides, with the chelating compounds of the formula Z, if appropriate in the presence of catalytic amounts of an alkali metal, such as Li or Na, also leads to the alcoholates, the hydrogen halide being split off. This reaction is generally carried out at temperatures of up to 200° C. and above.

(d) It is also possible to use the metal alcoholates, metalloid alcoholates and metal oxy-alcholates with lower, readily volatile alchols, such as methanol or ethanol, as the starting materials and to react these with a chelating compound of the formula Z, in which case the alcohol formed is removed by distillation. Alcoholates obtained by this route are, for example, the alcoholates of the metals Mg, Al, Sb, Ca, Ti and Sn or of the zirconyl cation.

(e) By reacting metal complexes, for example the acetylacetonates, with compounds of the formula Z with displacement of the ligand, for example acetylacetone, it is also possible to obtain the corresponding metal alcoholates, for example in the case of complexes of Ni, Cu, Zn and Sn-II.

(f) The action of complex-forming compounds of the formula Z on metal acetates, for example acetates of lead or bismuth, in many cases also gives the corresponding alcoholates, with removal of acetic acid.

(g) The complexed compounds, according to the invention, of the composition I in which X represents hydroxyl are also suitable as starting materials for the process according to the invention and, moreover, these compounds can themselves be manufactured by this process according to the invention.

(h) The basic metal alcoholates and metal oxy-alcoholates and also the compounds, according to the invention, of the composition I in which X represents hydroxyl can also be manufactured in situ as starting materials. For this purpose, the metal alcoholates, metalloid alcoholates or metal oxy-alcoholates obtained from 2 to 8 mols of a complex-forming compound of the formula Z and the metal are reacted with a stoichiometric amount of water or a less than equivalent amount of water, which is up to half the stoichiometric amount.

The process according to the invention can be carried out in various ways. In the case of the reaction of the virtually anhydrous proton-acids $H_nX^n$ with the abovementioned starting materials, the procedure is, in general, to add the anhydrous proton-acid, preferably in portions, to the starting materials. In this context, virtually anhydrous is understood to mean that only traces of moisture are present which do not have an adverse influence on the process according to the invention. Gaseous proton-acids, such as, for example, the hydrogen halides and hydrogen pseudohalides, are fed in continuously, preferably into solutions of the starting materials in hydrocarbons; exact metering (stoichiometric) is advantageous. Crystalline anhydrous proton-acids, such as, for example, phosphoric acid, are preferably added in the solid form, whilst liquid proton-acids, such as, for example, concentrated sulphuric acid, are also added in bulk, advantageously to a cooled solution of the alcoholate in petroleum ether. After the addition is complete, the reaction mixture is generally allowed to react further. Possible insoluble constituents can then be filtered off and the compound according to the invention can be isolated by the customary methods.

If the basic alcoholates and the compounds of the composition I in which X represents hydroxyl are manufactured in situ, either the water is added in the presence of an anhydrous compound $H_nX^n$, of an ammonium salt or of an acid anhydride, acid halide or acid ester, or the abovementioned starting materials are first manufactured and only then is the reagent for the introduction of the anion X added, without isolation of the starting materials formed.

The compounds of the composition I in which X represents hydroxyl are obtained by the process according to the invention by reacting the metal alcoholates, metal oxyalcoholates or metal dioxy-alcoholates obtained from the complexing compounds of the formula Z and the metals with a stoichiometric amount of water. This reaction is advantageously carried out in a hydrocarbon solvent, such as, for example, n-heptane, and at temperatures of up to 50° C., preferably at room temperature. Further solvents which are particularly suitable are hydrocarbons such as pentane, hexane, petroleum ether, octane, benzene or toluene.

In the case of the reaction with anhydrous proton-acids, the non-basic alcoholates are preferred as starting materials since, in this case, the desired compounds according to the invention are obtained direct when the solvent used is removed. However, the basic alcoholates or the compounds of the composition I in which X represents hydroxyl can also be employed without this giving rise to difficulties. It is necessary merely to remove the resulting water of reaction, preferably by azeotropic distillation. This reaction is therefore advantageously carried out using, as the solvent, hydrocarbons together with which the water can simultaneously be removed from the reaction mixture.

A large number of proton-acids of the formula $H_nX^n$ is known which can be manufactured in the anhydrous form. Crystalline proton-acids can contain water of crystallisation but this does not interfere in the process according to the invention and can be removed after the reaction. In addition to the proton-acids already mentioned $H_2[Fe(CN)_6]$, $H_2PtF_6$ and $HMn(CO)_5$ may be mentioned as examples from the category of inorganic complex acids.

Some of the proton-acids are instable or non-existent in the free form and it is therefore to be regarded as a considerable advantage of the process according to the invention that the anions of unstable acids can be introduced via their stable ammonium salts into the starting materials used according to the invention. However, this embodiment of the process according to the invention is not restricted to these ammonium salts but can be carried out in general with all ammonium salts. It should also be mentioned that the complexed acids, according to the invention, of the composition $H_nX^n \cdot qZ$ in general can also be used as the starting material, in place of the proton-acids $H_nX^n$, and this is highly advantageous, for example in the case of hypophosphorous acid and the hypophosphites.

In detail, the procedure with this embodiment is that the starting materials and the ammonium salts of the formula $A_nX^n$ are warmed together, the ammonia formed, the amine and the water of reaction, which is formed when the basic alcoholates and the composition I, according to the invention, in which X represents hydroxyl, are used, being driven out. The water is advantageously removed by azeotropic distillation. The non-basic alcoholates are preferably used as the starting material.

Amongst the ammonium salts, those which are especially suitable are those from which readily volatile amines are formed during the reaction. In the formula $A_nX^n$, A preferably represents $NH_4^\oplus$ or alkylammonium containing $C_1-C_4$-alkyl groups and especially containing $C_1-C_2$-alkyl groups. In particular, $NH_4^\oplus$ and monoalkyl-ammonium containing methyl and ethyl as alkyl are particularly preferred. The reaction temperature is up to 150° C. and preferably up to 110° C. The compounds according to the invention are isolated by means of customary methods.

In a further embodiment, the basic alcoholates and the compounds, according to the invention, of the composition I can also be reacted, as the starting materials, with acid anhydrides, acid halides and acid esters. This reaction can be carried out with or without a solvent and in general proceeds exothermically, so that additional warming of the reaction mixture is not necessary. In general, the acid ester, the acid halide and acid anhydride are added to the alcoholate all at once or in portions or, in the case of gases, continuously. The desired products are isolated by the customary methods. The reaction is best carried out at room temperature, with cooling if necessary.

Suitable acid anhydrides are, especially, the anhydrides of the organic acids and the acid-forming oxides of the elements C, N, P, S, Se, Cl, Br and I. Examples are: $CO_2$, $N_2O_5$, $P_2O_3$, $P_2O_5$, $SO_2$, $SO_3$, $SeO_3$, $Cl_2O_7$, $BrO_3$, $I_2O_5$, $N_2O_3$ or $I_2O_7$ as well as acetic anhydride, trifluoroacetic anhydride and benzoic anhydride. When mixed organic anhydrides, such as benzoic/acetic anhydride, are used, mixtures of compounds of the composition I in which X represents, for example, benzoate and acetate are obtained.

Suitable acid halides are, in particular, the chlorides and bromides. The acid components are preferably derived from the inorganic and organic acids and from the organic oxyacids of phosphorous and sulphur. Examples are: $SCl_2$, $S_2Cl_2$, $SeCl_2$, $SOCl_2$, $SO_2Cl_2$, $POCl_3$, $COCl_2$, $SO_2Br_2$, $POBr_3$, $CH_3COCl$, $C_6H_5COCl$, methylsulphonyl bromide and phenylphosphonyl chloride. In principle, mixtures of compounds of the composition I in which X represents halide and a further anion of an inorganic or organic acid are obtained when the acid halides are used.

In detail, this embodiment of the process according to the invention can be carried by adding the anhydrides or acid halides all at once or in portions to the starting materials and allowing the reaction mixture to react further in order to complete the reaction. The reaction is advantageously carried out using a solvent and at temperatures of up to 110° C., preferably at room temperature. The compounds, according to the invention, of the composition I are isolated by customary methods.

In another embodiment of the process according to the invention, the acid esters are used as reactants for introducing the anion X. A great advantage of this reaction is that it is possible in this way to introduce the anions X of the oxo acids, which are not stable in the free form. The esters of the inorganic and organic carboxylic acids, of the organic oxy-acids of the elements N, P, S, Se and the amphoteric elements and also of the organic oxy-acids of sulphur and phosphorus are particularly suitable. The esters are preferably derived from readily volatile aliphatic alcohols with 1 to 4 C atoms. In particular, the methyl esters and ethyl esters are used. The possible methods for manufacturing esters are known from the literature. In the case of the reaction of the esters of the amphoteric elements, the compounds, according to the invention, of the composition I in which X represents hydroxyl are preferably used as the starting materials. Examples of esters which may be mentioned are: dimethyl carbonate, diethyl carbonate, methyl orthocarbonate, dimethyl phosphite, dimethyl phosphate, dimethyl phosphonite, dimethyl phosphonate, diethyl sulphite, dimethyl sulphate, the methyl and ethyl esters of sulphonic acids and sulphinic acids, trimethyl arsenite, trimethyl arsenate, trimethyl antimonite, trimethyl antimonate, tetraethyl silicate, tetramethyl silicate, tetramethyl germanate, tetramethyl stannate, trimethyl borate and trimethyl aluminate, tetraethyl zirconate, tetramethyl titanate, dimethyl molybdate or dimethyl tungstate, diethyl chromate and trimethyl vanadate.

In order to carry out the reaction, the esters are added to the starting materials. The mixture is then preferably warmed and the alcohol formed is distilled off continuously and this can be accelerated by applying a vacuum. The reaction can be carried out with or without a solvent. After the reaction has ended, either the complex compounds according to the invention or solutions thereof are obtained, depending on the conditions, and these can be purified by the customary methods.

It is also possible to obtain, by this route, complex compounds of those oxy-acids which are derived from some non-metals and the amphoteric elements and tend to form condensed anions. Examples of such non-metals and elements which may be mentioned are P, As, Sb, Si, Ge, Sn, B, Al, Cr, Mo, W, V, Ti and Zr. Dimeric, trimeric and tetrameric to polymeric anions of different structures are known, for example, for such elements. Depending on the process of manufacture, these compositions according to the invention still contain acid ester bonds in the anions, for example when the ester of the oxo-acid which is used is hydrolysed with less than the equivalent amount of $H_2O$. In the case of the complete hydrolysis of the oxo-acid ester used, the corresponding ortho-anions are first formed and polyanions are formed from these by a condensation reaction, with removal of the water of reaction, preferably by means of azeotropic distillation. It is also possible for such condensation reactions already to proceed during hydrolysis. Thus, depending on the amount of water of reaction which is removed, various polyanions can form from one element, for example anions of the empirical formulae $SiO_3^{2-}$, $Si_2O_5^{2-}$ and $Si_3O_7^{2}$ from silicon, or also metaphosphate, metaborate, metaaluminate, metaarsenate, metatitanate, zirconates and metaantimonate. Depending on the degree of polycondensation of the anions, the products in this case are liquids of low viscosity to oily liquids or wax-like to resin-like solids. The latter can also serve as resins for the manufacture of mouldings, for example as casting resins.

Proton-oxy-acids can also be complexed by this process to give the composition I, according to the invention, if they are in the form of an ester (variant c) of the process according to the invention, by hydrolysing these esters in the presence of a complex-forming compound of the formula Z with stoichiometric amounts of water. Depending on the nature of the ester, various embodiments can be used.

If the esters are aliphatic or aromatic esters, preferably esters with lower alkanols which contain about 1 to 6, and preferably 1 to 2, C atoms, since these can be removed easily by distillation after the reaction, the ester is mixed with q mols of a complex-forming compound of the formula Z and the corresponding amount of $H_2O$ is added. The mixture is then stirred further until a homogeneous product is obtained and the alcohol which has formed is removed (distillation, if appropriate in vacuo). A condensation reaction, with removal of the water formed, can then follow, as described above, in order to manufacture the acids having oligomeric to polymeric anions. The reaction can be carried out without solvents or, preferably, with solvents, for example readily volatile ethers and in particular hydrocarbons. In general, the reaction is carried out at room temperature and the temperatures should preferably be not more than 50° C.

In another variant, the esters of the oxy-acids with q mols of a complex-forming compound Z are used as the starting materials and these are hydrolysed, optionally in the presence of solvents, with stoichiometric amounts of water. In other respects, the procedure can be as described above. The esters are readily accessible via transesterification reactions of, for example, alkyl esters of the oxy-acids with the complex-forming compounds of the formula Z.

The complexed compounds, according to the invention, of the composition I in which M denotes a proton are, in turn, outstandingly suitable as intermediate products for the manufacture of the metal salts and metalloid salts according to the process of the invention. For this purpose, the complexed acids of the formula $H_nX^n.pY.qZ$ are added, in accordance with the embodiments described above, to the basic or nonbasic alcoholates, and the alcohol formed is removed from the reaction mixture. Furthermore, it is possible to react metal oxides and metal hydroxides in this way, with removal of the water formed. The reaction temperature can be up to 150° C. and preferably up to 50°–100° C.

Possible starting components for the complexed acids according to the invention are the same acids as have been listed above for the metal salts, insofar as these acids have a $pK_a$ value of at most 11. In particular, the inorganic acids and the strong organic acids ($pK_a$ values of at least 4) are preferred. Preferably, these starting acids have $pK_a$ values of at most 7 and especially of at most 4.

In order to illustrate possible embodiments of the process according to the invention, reaction equations are given below by way of example. In these equations, Z represents the complex-forming compound which is formed from the alcoholate ligand Z′O when this takes up a proton.

(a) Alcoholate + anhydrous proton-acid

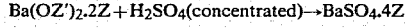

Ba(OZ′)$_2$.2Z + H$_2$SO$_4$(concentrated)→BaSO$_4$.4Z (b) Alcoholate + ammonium salt

Mg(OZ′)$_2$.2Z + 2NH$_4$F→MgF$_2$.4Z + 2NH$_3$ (c) Basic alcoholate + acid anhydride

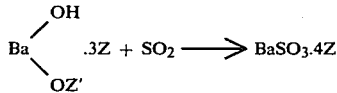

(d) Basic alcoholate + acid halide

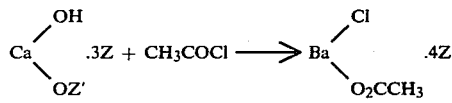

(e) Compound, according to the invention, of the composition I, in which X represents hydroxyl, + ester 2Ba(OH)$_2$.4Z + Si(OCH$_3$)$_4$→Ba$_2$SiO$_4$.8Z + 4CH$_3$OH (f) Ester with complex-forming compound + water

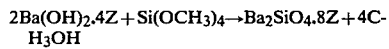

Si(OZ′)$_4$ + 4H$_2$O→Si(OH)$_4$.4Z (g) Ester + complex-forming compound + water

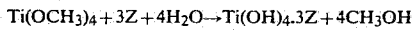

Ti(OCH$_3$)$_4$ + 3Z + 4H$_2$O→Ti(OH)$_4$.3Z + 4CH$_3$OH (h) Hydroxide + complexed proton-acid according to the invention

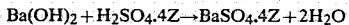

Ba(OH)$_2$ + H$_2$SO$_4$.4Z→BaSO$_4$.4Z + 2H$_2$O

It should also be mentioned that compounds, according to the invention, of the composition I which contain the anion of a volatile acid can be reacted with stronger nonvolatile anhydrous acids, in which case the readily volatile acid is displaced. Compounds according to the invention can be converted into other compounds according to the invention by this means. For example:

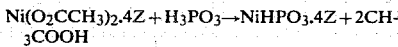

Ni(O$_2$CCH$_3$)$_2$.4Z + H$_3$PO$_3$→NiHPO$_3$.4Z + 2CH$_3$COOH

The complex compounds, according to the invention, of the composition I are of a crystalline or wax-like nature or are liquids of low viscosity to viscous liquids, depending on which anions, cations and complex compounds of the formula Z they contain and the ratio in which these are contained. They display a significant high stability to heat, which indicates that the complex-forming compounds of the formula Z are relatively firmly bonded. This statement is also supported by the fact that many representatives are crystalline compounds which can be recrystallised from suitable solvents without change in their composition. The 1,2,3-triol structural element and the glycerol monoether and monothioether structural element in the complexing compounds of the formula Z thus, apparently, display a surprisingly high affinity which ensures high stability and a broad field of application.

The compounds according to the invention are, in general, also surprisingly stable to air and moisture. Thus, even during manufacture, these compounds are not decomposed by the water formed, which, for example, is introduced into the reaction mixture as water of crystallisation of the inorganic salts. It is, therefore, also possible for a certain amount of water to remain in the compounds without this resulting in decomposition being observed. Conversely, up to a certain limit, water can also be added to anhydrous systems, no decomposition being observed and the solubility in non-polar solvents not being reduced. The compounds are destroyed by hydrolysis only when large amounts of water are added, especially when a solubilising additive, such as tetrahydrofurane, dioxane or methanol, is also used.

A particularly significant characteristic is the surprisingly good solubility of the compounds according to the invention in many organic solvents, even in non-polar aprotic solvents, such as the liquid hydrocarbons. The solubility can be influenced by the choice and the number of the complexing compounds of the formula Z. Thus, it has been found that compounds of the formula Z having branched radicals as a rule give compounds according to the invention which are of liquid consistency and with these compounds, in contrast to crystalline compounds, the solubility is then only a question of miscibility. The compatibility with natural and synthetic plastics is also very good.

Even when added in low concentrations, the compounds according to the invention surprisingly display an outstanding anti-static activity, which is superior to the activity of the known glycerol compounds which are used here as complexing compounds of the formula Z.

Because of their properties, the compounds according to the invention are outstandingly suitable for imparting anti-static characteristics to natural and synthetic polymers, lubricants and fuels and solutions and solvents based on hydrocarbons. The greatest activity is found in the case of the complexed proton-acids.

A further subject of the present invention is a mixture of substances containing a natural or synthetic polymer, a natural or synthetic lubricant or a fuel or a solution or a solvent, based on hydrocarbons, and a complexed compound of the composition I.

The mixtures preferably contain the compounds of the composition I in an amount of 0.001 to 15% by weight and preferably of 0.01 to 10, especially of 0.01 to 5 and in particular of 0.01 to 3% by weight.

Suitable thermoplastic polymers which can be used are, for example, the following thermoplastics:

1. Polymers which are derived from mono-unsaturated or bis-unsaturated hydrocarbons, such as polyolefines, such as, for example, polyethylene, which can optionally be crosslinked, polypropylene, polyisobutylene, polymethylbut-1-ene, polymethylpent-1-ene, polybut-1-ene, polyisoprene, polybutadiene, polystyrene and polyisobutylene, copolymers of the monomers on which the homopolymers mentioned are based, such as ethylene/propylene copolymers, propylene/isobutylene copolymers and styrene/butadiene copolymers, and also terpolymers of ethylene and propylene with a diene, such as, for example, hexadiene, dicyclopentadiene or ethylidenenorbornene, and mixtures of the abovementioned homopolymers, such as, for example, mixtures of polypropylene and polyethylene, of polypropylene and polybut-1-ene and of polypropylene and polyisobutylene.

2. Polyamides and copolyamides which are derived from diamines dicarboxylic acids and/or from aminocarboxylic acids or the corresponding lactams, such as polyamide 6, polyamide 6/6, polyamide 6/10, polyamide 11 and polyamide 12.

3. Polyesters which are derived from dicarboxylic acids and dialcohols and/or from hydroxycarboxylic acids or the corresponding lactones, such as polyethylene terephthalate, poly-1,4-dimethylol-cyclohexane terephthalate, polypivalolactone and poly-1,4-butylene terephthalate.

4. Polyacrylonitrile and also copolymers thereof with other vinyl compounds, such as acrylonitrile/-butadiene/styrene, acrylonitrile/styrene and acrylonitrile/styrene/acrylate copolymers. Further vinyl compounds for the formation of copolymers are: vinyl chloride, vinyl bromide and vinylidene chloride.

5. Plasticiser-free polyvinyl chloride, including plasticiser-free, chlorinated polyvinyl chloride, and also plasticiser-free copolymers of vinyl chloride, for example with vinyl acetate, and mixtures of these polymers with other copolymers and chlorinated polyolefines with a predominant content of vinyl chloride in the total mixture.

6. Plasticiser-containing polyvinyl chloride, also with the use of butadiene/acrylonitrile copolymers insofar as the proportion of vinyl chloride in the total mixture is predominant.

Plasticisers which can be used are: dibutyl phthalate, di-2-ethylhexyl phthalate, dibutyl sebacate, tributyl acetyl-citrate, tri-2-ethylhexyl acetyl-citrate, diphenyl 2-ethylhexyl phosphate, and alkylsulphonates ($C_{12}$–$C_{20}$) of phenol and of the cresols; and also polymeric plasticisers such as: adipic acid polyesters with 1,3-butanediol and hexanediol and adipic acid polyesters with 1,3- and/or 1,2-propanediol, in which the free OH groups are optionally acetylated.

7. Polyurethanes and polyurea.

8. Polyacetals, such as polyoxymethylene and polyoxyethylene, as well as those polyoxymethylenes which contain ethylene oxide as a comonomer.

Suitable natural polymers are, for example, vegetable and animal fibrous materials which can be processed to fabrics of all types. Examples are cotton, jute, hemp, sheep's wool, camel hair or silk.

Additives, such as plasticisers, heat stabilisers, antioxidants, dyestuffs, fillers, especially reinforcing fillers such as sized glass fibres, lubricants, light stabilisers and flameproofing agents, which are customarily used for processing and for improving the properties of these polymers can be added to the substrates before, after or together with the compounds, of the composition I, used according to the invention.

The incorporation of the substances to be used according to the invention can take place after the polymerisation, for example by mixing the substances and optionally further additives into the melt by the methods customary in the art, before or during shaping. The substances can also be incorporated in the form of a master batch, which contains these compounds, for example, in a concentration of 2.5 to 25% by weight, into the polymers to be provided with an anti-static finish.

The compounds, of the composition I, used according to the invention are also suitable for the external anti-static finishing of articles made of thermoplastic and thermosetting and natural polymers, especially of fibres, by spraying on or by the immersion process, using solutions. Suitable thermosetting plastics are, for example, epoxide resins, resins obtained from unsaturated dicarboxylic acid esters, melamine/formaldehyde resins, urea/formaldehyde resins, diallyl phthalate resins and phenol/formaldehyde resins. Suitable solvents for the compounds according to the invention are, in addition to the hydrocarbons, ethers, alcohols, esters, sulphones and acid amides.

Further suitable substrates for anti-static finishing are natural, for example mineral, and synthetic lubricants. The lubricants which can be used are commonly known to those skilled in the art and are described, for example, in "Schmiermittel Taschenbuch" ("Lubricants Handbook") (Hüthig Verlag, Heidelberg, 1974).

The lubricants can additionally contain other additives which are added in order to improve the properties, for example anti-corrosive agents, anti-oxidants, metal passivators, agents which improve the viscosity index, agents which lower the flow point, dispersing agents, detergents and other extreme pressure/anti-wear additives.

The fuels (motor fuels) based on hydrocarbons, which are suitable as substrates, are also commonly known to those skilled in the art. They can also contain further additives, such as, for example, anti-knock agents.

The compounds according to the invention can also be used for imparting anti-static characteristics to solutions or solvents based on hydrocarbons, such as pentane, hexane, heptane, cyclohexane, petroleum ether fractions, benzene, toluene or xylene, in order effectively to prevent the buildup of static charge due to friction in flow processes and the danger of explosion associated therewith.

A further field of application for the compounds according to the invention is the use for the surface treatment of glasses. A direct application to the surface can suffice, or it is possible, by means of after-treatment with heat, to effect a stronger fixing by, for example, chemical reactions. Suitable compounds are, for example, the titanium, tin, indium and antimony compounds of the composition I and especially those which contain fluoride or silicate anions.

The examples which follow serve to illustrate the present invention. In these examples parts are parts by weight and percentages are percentages by weight.

EXAMPLES

(I) Preparation Examples 1-204

The compounds listed in Table 1 were prepared according to one of the following processes A-$F_7$. The composition of the compounds according to the invention and some properties are also indicated in Table 1. The indices with a bar by the brackets in the glycerol compounds of the formula Z here indicate that these compounds are a statistical mixture. If different reaction temperatures or solvents have been used, this is indicated under Remarks in Table 1.

The values for the refractive index and the melting point can depend to a slight extent on the starting materials used and also on the purity of these materials.

Process A

A complexing compound of the formula Z and a metal salt are stirred at 120°-130° C. until a melt forms (up to 5 hours). The melt can then be taken up in a solvent, any turbidity can be filtered off and, in the case of crystalline compounds, the product can be recrystallised for purification. The yields are virtually quantitative. Losses in yield can result from the further purification operations.

Process B

A complexing compound of the formula Z and a metal salt etherate of diethyl ether are warmed to 100°-130° C. while stirring, until the ether which is liberated has been removed quantitatively in vacuo. Purification can be effected as in A. The yields are virtually quantitative. (This process is especially suitable in the case of an ansolvo-acid such as $BF_3$, $AlCl_3$, $MoCl_5$ and $SnCl_2$).

Process C

Using a rotary evaporator, a complexing compound of the formula Z and a metal salt containing water of crystallisation are warmed to 90°-100° C. under reduced pressure until the water of crystallisation has been removed quantitatively. Further purification can be effected as in A. The yields are virtually quantitative.

Process D

A complexing compound of the formula Z and the metal salt containing water of crystallisation are mixed with toluene or n-heptane and the mixture is then heated under reflux until the water of crystallisation has been removed quantitatively. The solvent is then distilled off under reduced pressure. Further purification can be effected as in A.

Process E

The anhydrous metal salt is dissolved in dimethylformamide and the complexing compound of the formula Z is added. The dimethylformamide is then distilled off at 60°-70° C. under an oil pump vacuum. The yields are virtually quantitative. Purification can be effected as in A.

Process $F_1$

A metal alcoholate with a complexing compound of the formula Z is prepared according to one of the processes a to f on pages and. An anhydrous proton-acid or water is then added to the mixture at 20°-30° C., while stirring well, in order to prepare the hydroxides (cooling is appropriate) and the reaction mixture is stirred for a further 30 minutes at 20°-30° C.

The solvent is then distilled off under reduced pressure. The yields are virtually quantitative. Purification can be effected as in A.

Process $F_2$

Water of reaction is removed from the system of a mixture consisting of a complexing compound of the formula Z, a metal hydroxide and toluene as the solvent, under reflux, while stirring, in an amount such that a basic alcoholate is formed.

An acid anhydride is then added to the mixture at 25° C. (gaseous acid anhydrides are passed in until the mixture is saturated).

The solvent is then distilled off under reduced pressure.

Purification can be effected as in A.

Process $F_3$

An alcoholate with a complexing compound of the formula Z and an ammonium salt are heated under reflux in heptane until all of the ammonia gas which is liberated has been driven out. The solvent is distilled off under reduced pressure. The yields are virtually quantitative.

Purification can be effected as in A.

Process $F_4$

Water is added to an alcoholate with a complexing compound of the formula Z, dissolved in heptane, in the stoichiometric amount which corresponds to the alcoholate. The mixture is stirred at 20° C. until the solution is homogeneous.

An acid ester is then added, the mixture is heated under reflux for 30 minutes and the solvent is distilled off under reduced pressure. The yields are virtually quantitative. In order to form polymeric anions ($SiO_3^-$, $Si_2O_5^{2-}$), the water of condensation is removed as an azeotrope.

Purification can be effected as in A.

Process $F_5$

A complexed metal carboxylate (metal acetate) or metal alcoholate with a compound of the formula Z is heated with an anhydrous proton-acid in heptane for some time under reflux. The solvent is then distilled off, together with the carboxylic acid (acetic acid), under reduced pressure. The final residues of solvent and carboxylic acid (acetic acid) are removed at 60° C. under an oil pump vacuum.

The yields are virtually quantitative. Purification can be effected as in A.

The anhydrous proton-acid can also be employed as a complex, according to the invention, of the composition I.

Process F$_6$

The acid to be complexed is introduced into a mixture of a complex-forming agent and a solvent (heptane or toluene) at 20° C. and the mixture is stirred until a clear solution is obtained. The solvent is then removed under reduced pressure. In the case of dilute aqueous acids (for example hypophosphorous acid), the water is removed in the presence of the complex-forming agent by azeotropic distillation.

Process F$_7$

Complexed $Si(OH)_4$ is prepared by hydrolysing tetramethyl orthosilicate in the presence of the complexing agent with a stoichiometric amount of water and distilling off methanol.

In order to prepare complexed $SiO_2.aq$ (silicic acid), $H_2O$ is added to tetramethyl orthosilicate, in the presence of the complexing agent, in an amount such that $SiO_2.aq$ must form (this would correspond to freshly precipitated silicic acid) and the methanol formed is distilled off.

TABLE 1

| Example | Composition of the complexed compound | | Number q | Prepared according to process | Remarks | Properties (melting point, refractive index) |
|---|---|---|---|---|---|---|
| | Salt | Compound of the formula Z | | | | |
| 1 | LiOH | i-$C_8H_{17}$—O—$CH_2$—CH—$CH_2$<br>       \|      \|<br>      OH   OH | 2 | A | Temperature = 70–80° C. | |
| 2 | $Na_2[S_2O_3]$ | i-$C_8H_{17}$—O—$CH_2$—CH—$CH_2$<br>       \|      \|<br>      OH   OH | 10 | E | $H_2O$/methanol as the solvent (sol) | $n_D^{20}$: 1.4621 |
| 3 | NaBr | i-$C_8H_{17}$—O—$CH_2$—CH—$CH_2$<br>       \|      \|<br>      OH   OH | 6 | E | Methanol as sol | $n_D^{20}$: 1.4578 |
| 4 | $Na_2[SO_4]$ | i-$C_8H_{17}$—O—$CH_2$—CH—$CH_2$<br>       \|      \|<br>      OH   OH | 4 | F$_1$ | | $n_D^{20}$: 1.4510 |
| 5 | KI | i-$C_8H_{17}$—O(—$CH_2$—$C_2H_3$—O—)$_2$H<br>                    \|<br>                   OH | 4 | E | Methanol as sol | $n_D^{20}$: 1.4753 |
| 6 | $Mg[S—CH_2—CH_2—CO_2]$ | i-$C_8H_{17}$—O—$CH_2$—CH—$CH_2$<br>       \|      \|<br>      OH   OH | 4 | F$_1$ | Without sol | $n_D^{20}$: 1.4658 |
| 7 | $Mg[O_2C—CH_3]_2$ | i-$C_8H_{17}$—O—$CH_2$—CH—$CH_2$<br>       \|      \|<br>      OH   OH | 4 | F$_1$ | | $n_D^{20}$: 1.4553 |
| 8 | $Mg[CNS]_2$ | i-$C_8H_{17}$—O—$CH_2$—CH—$CH_2$<br>       \|      \|<br>      OH   OH | 4 | F$_3$ | | $n_D^{20}$: 1.4795 |
| 9 | $MgF_2$ | i-$C_8$—$H_{17}$—O—$CH_2$—CH—$CH_2$<br>       \|      \|<br>      OH   OH | 4 | F$_3$ | | $n_D^{20}$: 1.4500 |
| 10 | $Mg[NO_3]_2$ | i-$C_8H_{17}$—O—$CH_2$—CH—$CH_2$<br>       \|      \|<br>      OH   OH | 4 | F$_3$ | | $n_D^{20}$: 1.4611 |
| 11 | MgS | i-$C_8H_{17}$—O—$CH_2$—CH—$CH_2$<br>       \|      \|<br>      OH   OH | 4 | F$_1$ | | $n_D^{20}$: 1.4662 |
| 12 | $Mg[HPO_3]$ | i-$C_8H_{17}$—O—$CH_2$—CH—$CH_2$<br>       \|      \|<br>      OH   OH | 4 | F$_1$ | | $n_D^{20}$: 1.4592 |
| 13 | $MgBr_2$ | n-$C_{18}H_{37}$—O$(CH_2$—$C_2H_3$—O$)$H<br>                    \|<br>                   OH   1 | 2 | D | | Melting point: 68–73° C. |
| 14 | $MgCl_2$ | n-$C_{12}H_{25}$—O—$CH_2$—CH—$CH_2$<br>       \|      \|<br>      OH   OH | 2 | D | | Melting point: 99–101° C. |

TABLE 1-continued

| Example | Composition of the complexed compound | | Number q | Prepared according to process | Remarks | Properties (melting point, refractive index) |
|---|---|---|---|---|---|---|
| | Salt | Compound of the formula Z | | | | |
| 15 | $MgBr_2$ | $n\text{-}C_{12}H_{25}\text{—}O\text{—}CH_2\text{—}\underset{OH}{CH}\text{—}\underset{OH}{CH_2}$ | 2 | D | | Melting point: 102–107° C. |
| 16 | $Mg[O_2C\text{—}CH_3]_2$ | $n\text{-}C_8H_{17}\text{—}O\text{—}CH_2\text{—}\underset{OH}{CH}\text{—}\underset{OH}{CH_2}$ | 2 | D | Chloroform as sol | $n_D^{20}$: 1.4553 |
| 17 | $MgCl_2$ | $n\text{-}C_{18}H_{37}\text{—}O\text{(}CH_2\text{—}\underset{OH}{C_2H_3}\text{—}O\text{)}_{\overline{1}}H$ | 4 | D | | Melting point: 65–68° C. |
| 18 | $Mg[S\text{—}CH_2\text{—}CO_2\text{—}i\text{-}C_{18}H_{17}]_2$ | $i\text{-}C_8H_{17}\text{—}O\text{—}CH_2\text{—}\underset{OH}{CH}\text{—}\underset{OH}{CH_2}$ | 4 | $F_1$ | Without sol | $n_D^{20}$: 1.4650 |
| 19 | $MgCl_2$ | $n\text{-}C_{18}H_{37}\text{—}O\text{(}CH_2\text{—}\underset{OH}{C_2H_3}\text{—}O\text{)}_{\overline{1}}H$ | 2 | D | | Melting point: >115° C. |
| 20 | $Ca[S\text{—}CH_2\text{—}CO_2\text{—}i\text{-}C_8H_{17}]_2$ | $i\text{-}C_8H_{17}\text{—}O\text{—}CH_2\text{—}\underset{OH}{CH}\text{—}\underset{OH}{CH_2}$ | 4 | $F_1$ | Without sol | $n_D^{20}$: 1.4748 |
| 21 | $Ca[S\text{—}CH_2\text{—}CH_2\text{—}CO_2]$ | $i\text{-}C_8H_{17}\text{—}O\text{—}CH_2\text{—}\underset{OH}{CH}\text{—}\underset{OH}{CH_2}$ | 4 | $F_1$ | | $n_D^{20}$: 1.4610 |
| 22 | CaS | $i\text{-}C_8H_{17}\text{—}O\text{—}CH_2\text{—}\underset{OH}{CH}\text{—}\underset{OH}{CH_2}$ | 4 | $F_1$ | | $n_D^{20}$: 1.4702 |
| 23 | $CaCl_2$ | $n\text{-}C_{18}H_{37}\text{—}O\text{(}CH_2\text{—}\underset{OH}{C_2H_3}\text{—}O\text{)}_{\overline{1}}H$ | 4 | A | | Melting point: 64–67° C. |
| 24 | $CaCl_2$ | $n\text{-}C_{18}H_{37}\text{—}O\text{(}CH_2\text{—}\underset{OH}{C_2H_3}\text{—}O\text{)}_{\overline{1}}H$ | 2 | A | | Melting point: 76–79° C. |
| 25 | $Ba[SO_4]$ | $i\text{-}C_8H_{17}\text{—}O\text{—}CH_2\text{—}\underset{OH}{CH}\text{—}\underset{OH}{CH_2}$ | 4 | $F_1$ | | $n_D^{20}$: 1.4610 |
| 26 | BaS | $i\text{-}C_8H_{17}\text{—}O\text{—}CH_2\text{—}\underset{OH}{CH}\text{—}\underset{OH}{CH_2}$ | 4 | $F_1$ | | $n_D^{20}$: 1.4602 |
| 27 | $BaBr_2$ | $i\text{-}C_8H_{17}\text{—}O\text{—}CH_2\text{—}\underset{OH}{CH}\text{—}\underset{OH}{CH_2}$ | 6 | E | | $n_D^{20}$: 1.4690 |
| 28 | $Ba[HPO_3]$ | $i\text{-}C_8H_{17}\text{—}O\text{—}CH_2\text{—}\underset{OH}{CH}\text{—}\underset{OH}{CH_2}$ | 6 | $F_1$ | | $n_D^{20}$: 1.4668 |
| 29 | $Ba_3[BO_3]_2$ | $i\text{-}C_8H_{17}\text{—}O\text{—}CH_2\text{—}\underset{OH}{CH}\text{—}\underset{OH}{CH_2}$ | 12 | $F_1$ | | $n_D^{20}$: 1.4676 |
| 30 | $Ba[CO_3]$ | $i\text{-}C_8H_{17}\text{—}O\text{—}CH_2\text{—}\underset{OH}{CH}\text{—}\underset{OH}{CH_2}$ | 4 | $F_2$ | | $n_D^{20}$: 1.4657 |
| 31 | $Ba[S\text{—}CH_2\text{—}CH_2\text{—}CO_2]$ | $i\text{-}C_8H_{17}\text{—}O\text{—}CH_2\text{—}\underset{OH}{CH}\text{—}\underset{OH}{CH_2}$ | 4 | $F_1$ | | $n_D^{20}$: 1.4716 |
| 32 | $Ba[S\text{—}CH_2\text{—}CO_2\text{—}i\text{-}C_8H_{17}]$ | $i\text{-}C_8H_{17}\text{—}O\text{—}CH_2\text{—}\underset{OH}{CH}\text{—}\underset{OH}{CH_2}$ | 2 | $F_1$ | | |
| 33 | $Ba[SO_3]$ | $i\text{-}C_8H_{17}\text{—}O\text{—}CH_2\text{—}\underset{OH}{CH}\text{—}\underset{OH}{CH_2}$ | 4 | $F_2$ | | $n_D^{20}$: 1.4667 |

TABLE 1-continued

| Example | Composition of the complexed compound | | Number q | Prepared according to process | Remarks | Properties (melting point, refractive index) |
|---|---|---|---|---|---|---|
| | Salt | Compound of the formula Z | | | | |
| 34 | $Ba[S-CH_2-CO_2-i-C_8H_{17}]_2$ | $n-C_8H_{17}-O-CH_2-\underset{OH}{CH}-\underset{OH}{CH_2}$ | 4 | $F_1$ | | $n_D^{20}$: 1.4750 |
| 35 | $Ba[S-CH_2-CH_2-CO_2]$ | $n-C_8H_{17}-O-CH_2-\underset{OH}{CH}-\underset{OH}{CH_2}$ | 4 | $F_1$ | | $n_D^{20}$: 1.4745 |
| 36 | $Ba_2[SiO_4]$ | $i-C_8H_{17}-O-CH_2-\underset{OH}{CH}-\underset{OH}{CH_2}$ | 8 | $F_4$ | | $n_D^{20}$: 1.4685 |
| 37 | $Ba[HPO_4]$ | $i-C_8H_{17}-O-CH_2-\underset{OH}{CH}-\underset{OH}{CH_2}$ | 4 | $F_1$ | | $n_D^{20}$: 1.4680 |
| 38 | $AlCl_3$ | $n-C_{18}H_{37}-O{\left(CH_2-\underset{OH}{C_2H_3}-O\right)}_{\overline{1}}H$ | 4 | B | | Melting point: 64–66° C. |
| 39 | $AlCl_3$ | $n-C_{18}H_{37}-O{\left(CH_2-\underset{OH}{C_2H_3}-O\right)}_{\overline{1}}H$ | 8 | A | | Melting point: 61–63° C. |
| 40 | $AlCl_3$ | $n-C_{18}H_{37}-O{\left(CH_2-\underset{OH}{C_2H_3}-O\right)}_{\overline{1}}H$ | 4 | A | | Melting point: 62–65° C. |
| 41 | $TiCl_4$ | $n-C_{18}H_{37}-O{\left(CH_2-\underset{OH}{C_2H_3}-O\right)}_{\overline{1}}H$ | 8 | A | | Melting point: 59–62° C. |
| 42 | $TiCl_4$ | $n-C_{18}H_{37}-O{\left(CH_2-\underset{OH}{C_2H_3}-O\right)}_{\overline{1}}H$ | 4 | A | | Melting point: 60–62° C. |
| 43 | $ZrOCl_2$ | $n-C_{18}H_{37}-O{\left(CH_2-\underset{OH}{C_2H_3}-O\right)}_{\overline{1}}H$ | 4 | D | | Melting Point: 60–62° C. |
| 44 | $CrCl_3$ | $i-C_5H_{11}-O-CH_2-\underset{OH}{CH}-\underset{OH}{CH_2}$ | 6 | D | n-Heptane as sol | deeply colored |
| 45 | $CrCl_3$ | $i-C_8H_{17}-O-CH_2-\underset{OH}{CH}-\underset{OH}{CH_2}$ | 4 | D | n-Heptane as sol | |
| 46 | $MoCl_5$ | (bicyclic)$-CH_2-O-CH_2-\underset{OH}{CH}-\underset{OH}{CH_2}$ | 4 | B | | |
| 47 | $MnCl_2$ | $n-C_{18}H_{37}-O{\left(CH_2-\underset{OH}{C_2H_3}-O\right)}_{\overline{1}}H$ | 4 | A | | Melting point: 62–64° C. |
| 48 | $FeCl_2$ | $n-C_{12}H_{25}-O-CH_2-\underset{OH}{CH}-\underset{OH}{CH_2}$ | 2 | D | | Melting point: 59–64° C. |
| 49 | $FeCl_2$ | $i-C_8H_{17}-O-CH_2-\underset{OH}{CH}-\underset{OH}{CH_2}$ | 4 | D | Petroleum ether as sol | $n_D^{20}$: 1.4775 |
| 50 | $FeCl_2$ | $n-C_9H_{19}-\text{(phenyl)}-O{\left(CH_2-\underset{OH}{C_2H_3}-O\right)}_{\overline{3}}H$ | 4 | D | | deeply red-brown colored |
| 51 | $FeCl_3$ | $n-C_{12}H_{25}-O{\left(CH_2-\underset{OH}{C_2H_3}-O\right)}_{\overline{3}}H$ | 4 | A | | |

TABLE 1-continued

| Example | Composition of the complexed compound | | Number q | Prepared according to process | Remarks | Properties (melting point, refractive index) |
|---|---|---|---|---|---|---|
| | Salt | Compound of the formula Z | | | | |
| 52 | $Co[O_2C-CH_3]_2$ | $n\text{-}C_{18}H_{37}-O+CH_2-C_2H_3-O+H$<br>        $\|$<br>       $OH$  $\bar{1}$ | 4 | D | | Melting point: 56–58° C. |
| 53 | $Co[O_2C-CH_3]_2$ | $tert.\text{-}C_{12}H_{25}-S-CH_2-CH-CH_2$<br>                      $\|$     $\|$<br>                     $OH$  $OH$ | 4 | D | n-Heptane as sol | Violet coloured |
| 54 | $Ni[HPO_3]$ | $i\text{-}C_8H_{17}-O-CH_2-CH-CH_2$<br>                      $\|$     $\|$<br>                     $OH$  $OH$ | 4 | $F_5$ | | $n_D^{20}$: 1.4638 |
| 55 | $Ni[O_2C-CH_3]_2$ | $n\text{-}C_{18}H_{37}-O+CH_2-C_2H_3-O+H$<br>        $\|$<br>       $OH$  $\bar{1}$ | 4 | D | | Melting point: 56–58° C. |
| 56 | $NiCl_2$ | $n\text{-}C_{12}H_{25}-O-CH_2-CH-CH_2$<br>                      $\|$     $\|$<br>                     $OH$  $OH$ | 2 | D | | Melting point: 112–116° C. |
| 57 | $Mg_3(BO_3)_2$ | $i\text{-}C_8H_{17}-O-CH_2-CH-CH_2$<br>                      $\|$     $\|$<br>                     $OH$  $OH$ | 12 | $F_1$ | | |
| 58 | $NiCl_2$ | $i\text{-}C_8H_{17}-O-CH_2-CH-CH_2$<br>                      $\|$     $\|$<br>                     $OH$  $OH$ | 2 | D | Petroleum ether as sol | Wax-like |
| 59 | $NiCl_2$ | $i\text{-}C_8H_{17}-O-CH_2-CH-CH_2$<br>                      $\|$     $\|$<br>                     $OH$  $OH$ | 4 | D | Petroleum ether as sol | Colour, green |
| 60 | $Ni[O_2C-CH_3]_2$ | $n\text{-}C_{12}H_{25}-O-CH_2-CH-CH_2$<br>                      $\|$     $\|$<br>                     $OH$  $OH$ | 4 | D | n-Heptane as sol | Melting point: 42–45° C. |
| 61 | $CuCl_2$ | $i\text{-}C_8H_{17}-O-CH_2-CH-CH_2$<br>                      $\|$     $\|$<br>                     $OH$  $OH$ | 4 | D | n-Heptane as sol | |
| 62 | $Cu[SO_4]$ | $i\text{-}C_8H_{17}-O-CH_2-CH-CH_2$<br>                      $\|$     $\|$<br>                     $OH$  $OH$ | 5 | E | Dimethylformamide as the solvent | $n_D^{20}$: 1.4638 |
| 63 | $Cu[SO_4]$ | $i\text{-}C_8H_{17}-O-CH_2-CH-CH_2$<br>                      $\|$     $\|$<br>                     $OH$  $OH$ | 5 | E | Methanol as the solvent | $n_D^{20}$: 1.4633 |
| 64 | $Cu[NO_3]_2$ | $i\text{-}C_8H_{17}-O-CH_2-CH-CH_2$<br>                      $\|$     $\|$<br>                     $OH$  $OH$ | 4 | D | n-Hexane as sol | $n_D^{20}$: 1.4663 |
| 65 | $Cu[NO_3]_2$ | $n\text{-}C_5H_{11}-O-CH_2-CH-CH_2$<br>                      $\|$     $\|$<br>                     $OH$  $OH$ | 4 | D | n-Heptane as sol | |
| 66 | $Ag[NO_3]$ | $i\text{-}C_8H_{17}O+CH_2-CHCH_2O)_2H$<br>                      $\|$<br>                     $OH$ | 5 | E | | $n_D^{20}$: 1.4658 |
| 67 | $Ag[NO_3]$ | $i\text{-}C_{13}H_{27}-O-CH_2-CH-CH_2$<br>                      $\|$     $\|$<br>                     $OH$  $OH$ | 6 | E | | $n_D^{20}$: 1.4620 |
| 68 | $ZnCl_2$ | $i\text{-}C_8H_{17}-O-CH_2-CH-CH_2$<br>                      $\|$     $\|$<br>                     $OH$  $OH$ | 3 | A | | |
| 69 | $ZnCl_2$ | $n\text{-}C_{18}H_{37}-O+CH_2-C_2H_3-O+H$<br>        $\|$<br>       $OH$  $\bar{1}$ | 4 | A | | Melting point: 61–63° C. |
| 70 | $ZnCl_2$ | $n\text{-}C_{18}H_{37}-O+CH_2-C_2H_3-O+H$<br>        $\|$<br>       $OH$  $\bar{1}$ | 2 | A | | Melting point: 60–62° C. |

TABLE 1-continued

| Example | Composition of the complexed compound | | Number q | Prepared according to process | Remarks | Properties (melting point, refractive index) |
|---|---|---|---|---|---|---|
| | Salt | Compound of the formula Z | | | | |
| 71 | $Zn[HPO_4]$ | tert.-$C_{12}H_{25}$—S—$CH_2$—CH—$CH_2$<br>                                                 OH   OH | 4 | $F_1$ | | $n_D^{20}$: 1.4955 |
| 72 | $Zn[S—CH_2—CO_2—i-C_8H_{17}]_2$ | i-$C_8H_{17}$—O—$CH_2$—CH—$CH_2$<br>                                OH   OH | 4 | $F_1$ | Without sol | $n_D^{20}$: 1.4731 |
| 73 | $Zn[SO_3]$ | i-$C_8H_{17}$—O—$CH_2$—CH—$CH_2$<br>                                OH   OH | 4 | $F_2$ | n-Heptane as sol | $n_D^{20}$: 1.4668 |
| 74 | $ZnCl_2$ | n-$C_{18}H_{37}$—O$(CH_2$—$C_2H_3$—O$)_{\overline{1}}$H<br>                                OH | 2 | A | | Melting point: 57–59° C. |
| 75 | $ZnBr_2$ | n-$C_{18}H_{37}$—O$(CH_2$—$C_2H_3$—O$)_{\overline{1}}$H<br>                                OH | 2 | A | | Melting point: 53–55° C. |
| 76 | $ZnCl_2$ | i-$C_8H_{17}$—O—$CH_2$—CH—$CH_2$<br>                                OH   OH | 2 | A | | $n_D^{20}$: 1.4770 |
| 77 | $ZnCl_2$ | i-$C_8H_{17}$—O—$CH_2$—CH—$CH_2$<br>                                OH   OH | 4 | A | | $n_D^{20}$: 1.4648 |
| 78 | $Cd[O_2C—CH_3]_2$ | i-$C_{13}H_{27}$—O—$CH_2$—CH—$CH_2$<br>                                OH   OH | 6 | E | | $n_D^{20}$: 1.4642 |
| 79 | $BF_3$ | n-$C_{18}H_{37}$—O$(CH_2$—$C_2H_3$—O$)_{\overline{1}}$H<br>                                OH | 4 | B | | Melting point: 58–60° C. |
| 80 | $BF_3$ | n-$C_{18}H_{37}$—O$(CH_2$—$C_2H_3$—O$)_{\overline{1}}$H<br>                                OH | 2 | B | | Melting point: 57–59° C. |
| 81 | $BF_3$ | i-$C_{13}H_{27}$—O—$CH_2$—CH—$CH_2$<br>                                OH   OH | 2 | B | | $n_D^{20}$: 1.4500 |
| 82 | $SiCl_4$ | n-$C_{12}H_{25}$—S—$CH_2$—CH—$CH_2$<br>                                OH   OH | 4 | $F_1$ | | |
| 83 | $Sn[S—CH_2—CH_2—CO_2]_2$ | i-$C_8H_{17}$—O—$CH_2$—CH—$CH_2$<br>                                OH   OH | 4 | $F_1$ | | $n_D^{20}$: 1.4858 |
| 84 | $SnCl_4$ | i-$C_8H_{17}$—O—$CH_2$—CH—$CH_2$<br>                                OH   OH | 6 | B | | $n_D^{20}$: 1.4688 |
| 85 | $SnCl_4$ | i-$C_8H_{17}$—O—$CH_2$—CH—$CH_2$<br>                                OH   OH | 4 | B | | $n_D^{20}$: 1.4760 |
| 86 | $Sn[S—CH_2—CO_2—i-C_8H_{17}]_4$ | i-$C_8H_{17}$—O—$CH_2$—CH—$CH_2$<br>                                OH   OH | 4 | $F_1$ | | $n_D^{20}$: 1.4787 |
| 87 | $Sn[S—CH_2—CH_2—CO_2—i-C_8H_{17}]_2$ | i-$C_8H_{17}$—O—$CH_2$—CH—$CH_2$<br>                                OH   OH | 4 | $F_1$ | | |
| 88 | $SnCl_4$ | n-$C_{12}H_{25}$—O—$CH_2$—CH—$CH_2$<br>                                OH   OH | 2 | B | | Melting point: 51–55° C. |
| 89 | $SnBr_2$ | n-$C_{18}H_{37}$—O$(CH_2$—$C_2H_3$—O$)_{\overline{1}}$H<br>                                OH | 2 | D | | Melting point: 50–53° C. |

TABLE 1-continued

| Example | Salt | Compound of the formula Z | Number q | Prepared according to process | Remarks | Properties (melting point, refractive index) |
|---|---|---|---|---|---|---|
| 90 | $SnCl_4$ | $n\text{-}C_{18}H_{37}\text{—}O\text{+}CH_2\text{—}C_2H_3\text{—}O\text{+}H$ <br> $\quad\quad\quad\quad\quad\quad\quad\quad\quad \vert \quad\quad \overline{1}$ <br> $\quad\quad\quad\quad\quad\quad\quad\quad\quad OH$ | 4 | A | | Melting point: 51–54° C. |
| 91 | $SnCl_4$ | $n\text{-}C_{18}H_{37}\text{—}O\text{+}CH_2\text{—}C_2H_3\text{—}O\text{+}H$ <br> $\quad\quad\quad\quad\quad\quad\quad\quad OH \quad \overline{1}$ | 2 | A | | Melting point: 50–53° C. |
| 92 | $SnCl_4$ | $n\text{-}C_{18}H_{37}\text{—}O\text{+}CH_2\text{—}C_2H_3\text{—}O\text{+}H$ <br> $\quad\quad\quad\quad\quad\quad\quad\quad OH \quad \overline{1}$ | 8 | A | | Melting point: 54–57° C. |
| 93 | $SnCl_2$ | $n\text{-}C_8H_{17}\text{—}O\text{+}CH_2\text{—}C_2H_3\text{—}O\text{+}H$ <br> $\quad\quad\quad\quad\quad\quad\quad\quad OH \quad \overline{1}$ | 4 | D | | $n_D^{20}$: 1.4768 |
| 94 | $SnCl_2$ | $n\text{-}C_{18}H_{37}\text{—}O\text{+}CH_2\text{—}C_2H_3\text{—}O\text{+}H$ <br> $\quad\quad\quad\quad\quad\quad\quad\quad OH \quad \overline{1}$ | 4 | D | | Melting point: 55–58° C. |
| 95 | $SnBr_2$ | $i\text{-}C_8H_{17}\text{—}O\text{—}CH_2\text{—}CH\text{—}CH_2$ <br> $\quad\quad\quad\quad\quad\quad\quad\quad\quad\quad OH \quad OH$ | 4 | A | | $n_D^{20}$: 1.4852 |
| 96 | $Pb[SO_4]$ | $i\text{-}C_8H_{17}\text{—}O\text{—}CH_2\text{—}CH\text{—}CH_2$ <br> $\quad\quad\quad\quad\quad\quad\quad\quad\quad\quad OH \quad OH$ | 4 | $F_1$ | | $n_D^{20}$: 1.4610 |
| 97 | $Sb[S\text{—}CH_2\text{—}CO_2\text{—}i\text{-}C_8H_{17}]_3$ | $i\text{-}C_8H_{17}\text{—}O\text{—}CH_2\text{—}CH\text{—}CH_2$ <br> $\quad\quad\quad\quad\quad\quad\quad\quad\quad\quad OH \quad OH$ | 3 | $F_1$ | Without sol | $n_D^{20}$: 1.4892 |
| 98 | $Sb_2[S\text{—}CH_2\text{—}CH_2\text{—}CO_2]_3$ | $i\text{-}C_8H_{17}\text{—}O\text{—}CH_2\text{—}CH\text{—}CH_2$ <br> $\quad\quad\quad\quad\quad\quad\quad\quad\quad\quad OH \quad OH$ | 6 | $F_1$ | Without sol | $n_D^{20}$: 1.5002 |
| 99 | $SbCl_5$ | $n\text{-}C_{18}H_{37}\text{—}O\text{+}CH_2\text{—}C_2H_3\text{—}O\text{+}H$ <br> $\quad\quad\quad\quad\quad\quad\quad\quad OH \quad \overline{1}$ | 4 | A | | Melting point: 51–53° C. |
| 100 | $SbCl_5$ | $n\text{-}C_{18}H_{37}\text{—}O\text{+}CH_2\text{—}C_2H_3\text{—}O\text{+}H$ <br> $\quad\quad\quad\quad\quad\quad\quad\quad OH \quad \overline{1}$ | 2 | A | | Melting point: 48–51° C. |
| 101 | $SbCl_3$ | $n\text{-}C_{18}H_{37}\text{—}O\text{+}CH_2\text{—}C_2H_3\text{—}O\text{+}H$ <br> $\quad\quad\quad\quad\quad\quad\quad\quad OH \quad \overline{5}$ | 4 | A | | Melting point: 52–55° C. |
| 102 | $Ce[NO_3]_3$ | $i\text{-}C_8H_{17}\text{—}O\text{—}CH_2\text{—}CH\text{—}CH_2$ <br> $\quad\quad\quad\quad\quad\quad\quad\quad\quad\quad OH \quad OH$ | 4 | D | n-Heptane as sol | $n_D^{20}$: 1.4844 |
| 103 | $CeCl_3$ | " | 4 | D | n-Heptane as sol | $n_D^{20}$: 1.433 |
| 104 | $Ba[O_3S\text{—}CF_3]_2$ | " | 4 | $F_1$ | | |
| 105 | $Mg_2[TiO_4]$ | " | 8 | $F_4$ | | |
| 106 | $CaF_2$ | " | 4 | $F_1$ | | $n_D^{20}$: 1.4512 |
| 107 | $Si[O_3S\text{—}CF_3]_4$ | " | 4 | $F_1$ | | |
| 108 | $Mg[NO_3]_2$ | $i\text{-}C_8H_{17}\text{—}O\text{—}CH_2\text{—}CH\text{—}CH_2$ <br> $\quad\quad\quad\quad\quad\quad\quad\quad\quad\quad OH \quad OH$ | 4 | $F_1$ | | $n_D^{20}$: 1.4573 |
| 109 | $AlCl_3$ | " | 4 | B | | $n_D^{20}$: 1.472 |
| 110 | $MnBr_2$ | " | 4 | A | | $n_D^{20}$: 1.4772 |
| 111 | $Fe_2(SO_4)_3$ | " | 10 | $F_1$ | | Colour, red-brown |
| 112 | $FePO_4$ | " | 5 | $F_1$ | | Colour, red-brown |
| 113 | $Fe(NO_3)_3$ | " | 5 | $F_1$ | | Colour, red-brown |
| 114 | $Zn_3(BO_3)_2$ | " | 12 | $F_1$ | | $n_D^{20}$: 1.4648 |
| 115 | $Mg(OH)_2$ | " | 4 | $F_1$ | Reaction temperature 50° C. | Highly viscous mass |

TABLE 1-continued

| Example | Composition of the complexed compound | | Number q | Prepared according to process | Remarks | Properties (melting point, refractive index) |
|---|---|---|---|---|---|---|
| | Salt | Compound of the formula Z | | | | |
| 116 | Mg(HPO$_4$) | '' | 4 | F$_1$ | | $n_D^{20}$: 1.4585 |
| 117 | MgBr$_2$ | '' | 4 | D | | Turbid viscous solution |
| 118 | FeCl$_3$ | '' | 4 | D | | Red-brown liquid |
| 119 | MgCl$_2$ | '' | 4 | D | | $n_D^{20}$: 1.4656 |
| 120 | InCl$_3$ | '' | 4 | A | | $n_D^{20}$: 1.475 |
| 121 | Th(NO$_3$)$_4$ | '' | 4 | D | | $n_D^{20}$: 1.4815 |
| 122 | BiCl$_3$ | '' | 4 | A | | $n_D^{20}$: 1.4853 |
| 123 | HgCl$_2$ | '' | 4 | A | | $n_D^{20}$: 1.463 |
| 124 | Ba(Si$_2$O$_5$) | '' | 4 | F$_4$ | | |
| 125 | Ba(SiO$_3$) | '' | 4 | F$_4$ | | |
| 126 | BeCl$_2$ | '' | 4 | A | | $n_D^{20}$: 1.4609 |
| 127 | NbCl$_5$ | '' | 4 | A | | $n_D^{20}$: 1.490 |
| 128 | YCl$_3$ | '' | 4 | A | | $n_D^{20}$: 1.478 |
| 129 | BF$_3$ | '' | 1 | B | soluble only in toluene | $n_D^{20}$: 1.4268 |
| 130 | SnCl$_4$ | '' | 1 | B | | $n_D^{20}$: 1.5062 |
| 131 | Mg(SiO$_3$) | CX$_1$ | 4 | F$_4$ | | |
| 132 | Mg(Si$_3$O$_7$) | CX$_1$ | 2 | F$_4$ | | |
| 133 | Mg(OH)$_2$ | CX$_1$ | 3 | F$_1$ | | |
| 134 | AlCl$_3$ | CX$_1$ | 2 | B | n-heptane as sol | Cl determination 11.0% (19.6) |
| 135 | FeCl$_3$ | CX$_1$ | 2 | D | | |
| 136 | TiCl$_4$ | CX$_1$ | 2 | A | | Cl determination 10.6% (23.7) |
| 137 | Cd(O$_2$CCH$_3$)$_2$ | CX$_1$ | 6 | E | | $n_D^{20}$: 1.4558 |
| 138 | CdCl$_2$ | CX$_4$ | 5 | E | methanol/H$_2$O as sol | $n_D^{20}$: 1.4667 |
| 139 | Mg(H$_2$PO$_2$)$_2$ | CX$_1$ | 4 | F$_5$ | | |
| 140 | Mg(H$_2$PO$_2$)$_2$ | CX$_4$ | 4 | F$_5$ | | $n_D^{20}$: 1.4649 |
| 141 | Ca(H$_2$PO$_2$)$_2$ | CX$_4$ | 4 | F$_5$ | | $n_D^{20}$: 1.4614 |
| 142 | Ca(SCN)$_2$ | CX$_4$ | 3 | F$_3$ | | |
| 143 | Mg(SiO$_3$) | CX$_4$ | 3 | F$_4$ | | $n_d^{20}$: 1.4658 |
| 144 | NaO$_2$C—CH$_3$ | CX$_1$ | 5 | E | n-heptane/methanol as sol | $n_D^{20}$: 1.4512 |
| 145 | Mg(HPO$_3$) | CX$_4$ | 3 | F$_5$ | | $n_D^{20}$: 1.4645 |
| 146 | Ca(HPO$_3$) | CX$_4$ | 3 | F$_5$ | | $n_D^{20}$: 1.465 |
| 147 | Mg(SO$_3$) | CX$_4$ | 3 | F$_2$ | | $n_D^{20}$: 1.4683 |
| 148 | Ca(SO$_3$) | CX$_4$ | 3 | F$_2$ | | |
| 149 | Ni(SiO$_3$) | CX$_4$ | 3 | F$_5$ | | |
| 150 | Ba(HPO$_3$) | CX$_3$ | 4 | F$_5$ | | melting point: |
| 151 | ZnCl$_2$ | CX$_3$ | 2 | A | | melting point: 59–62° C. |
| 152 | SiCl$_4$ | CX$_3$ | 2 | A | | Cl determination 2.2% (16.5) |
| 153 | MgCl$_2$ | CX$_3$ | 2 | D | | melting point: 125–28° C. |
| 154 | CaCl$_2$ | CX$_3$ | 2 | A | | melting point: 75–78° C. |
| 155 | CaCl$_2$ | CX$_3$ | 3 | A | | melting point: 70–72° C. |
| 156 | MgCl$_2$ | CX$_3$ | 3 | D | | melting point: 71–73° C. |
| 157 | Mg(O$_2$C—CH$_3$)$_2$ | CX$_3$ | 3 | E | methanol as sol | melting point: 56–58° C. |
| 158 | Ba(SO$_4$) | CX$_2$ | 3 | F$_1$ | | |
| 159 | MnBr$_2$ | CX$_4$ | 2 | D | | $n_D^{30}$: 1.490 |
| 160 | SnCl$_4$·1.33 MgCl$_2$ | CX$_3$ | 4 | D | | melting point: 63–66° C. |
| 161 | Mg(Si$_2$O$_5$) | CX$_3$ | 4 | F$_4$ | | melting point: 53–55° C. |
| 162 | Ca(Si$_3$O$_7$) | CX$_3$ | 4 | F$_4$ | | melting point: 54–56° C. |
| 163 | Ca(TiO$_3$) | CX$_3$ | 4 | F$_4$ | | melting point: 58–61° C. |
| 164 | Ca(SO$_3$) | CX$_3$ | 2 | F$_2$ | | melting point: 53–57° C. |
| 165 | Ni(HPO$_3$) | CX$_3$ | 2 | F$_5$ | | melting point: 54–58° C. |
| 166 | Mn(HPO$_3$) | CX$_3$ | 2 | F$_5$ | | melting point: 53–57° C. |
| 167 | Mn(H$_2$PO$_2$)$_2$ | CX$_3$ | 2 | F$_5$ | | melting point: 54–58° C. |
| 168 | Mn(H$_2$PO$_3$)$_2$ | CX$_3$ | 2 | F$_5$ | | melting point: |

TABLE 1-continued

| Example | Composition of the complexed compound | | Number q | Prepared according to process | Remarks | Properties (melting point, refractive index) |
|---|---|---|---|---|---|---|
| | Salt | Compound of the formula Z | | | | |
| 169 | $B(OCH_3)_3$ | $CX_3$ | 2 | A | | 60-66° C. melting point: 55-60° C. |
| 170 | $Fe_2(SiO_3)_3$ | $CX_3$ | 2 | $F_5$ | | |
| 171 | $AlCl_3$ | $CX_3$ | 2 | B | methanol as sol | melting point: 65-67° C. Cl determination 8.1% (12.9%) |
| 172 | $AlCl_3$ | $CX_3$ | 4 | B | methanol as sol | melting point: 65-67° C. Cl determination 3.9% (7.0%) |
| 173 | $TiCl_4$ | $CX_3$ | 4 | B | | melting point: 65-63° C. Cl determination 6.0% (9.0%) |
| 174 | $TiCl_4$ | $CX_3$ | 2 | B | | Cl determination 9.0% (16.1%) |
| 175 | $Ni(SiO_3)$ | $CX_3$ | 3 | $F_5$ | | melting point: 52-54° C. |
| 176 | $Ca(H_2PO_3)_2$ | $CX_3$ | 3 | $F_5$ | | melting point: 61-63° C. |
| 177 | $Ca(OB=O)_2$ | $CX_3$ | 3 | $F_1$ | | melting point: 51-53° C. |
| 178 | $Ca(H_2PO_2)_2$ | $CX_3$ | 3 | $F_5$ | | melting point: 61-65° C. |
| 179 | $Mg(SiO_3)$ | $CX_3$ | 2 | $F_4$ | | melting point: 56-58° C. |
| 180 | $Ca(NO_3)_2$ | $CX_2$ | 3 | D | | |
| 181 | $Ni(TiO_3)$ | $CX_3$ | 2 | $F_5$ | | polymer |
| 182 | $Ca(ZrO_3)$ | $CX_3$ | 2 | $F_4$ | | polymer |
| 183 | $Ca(SiO_3)$ | $CX_3$ | 2 | $F_4$ | | polymer |
| 184 | $Ba(HPO_4)$ | $CX_3$ | 3 | $F_5$ | | melting point: 58-62° C. |
| 185 | $PbO$ | $CX_3$ | 2 | $F_1$ | | melting point: 49-51° C. |
| 186 | $Zn(H_2PO_3)_2$ | $CX_3$ | 3 | $F_5$ | | melting point: 50-54° C. |
| 187 | $Zn(H_2PO_2)_2$ | $CX_3$ | 3 | $F_5$ | | melting point: 56-61° C. |
| 188 | $H_3PO_2$ | $CX_1$ | 1 | $F_6$ | | $n_D^{20}$: 1.453 |
| 189 | $H_3PO_2$ | $CX_4$ | 1 | $F_6$ | | $n_D^{20}$: 1.4608 |
| 190 | $H_3PO_2$ | $CX_3$ | 1 | $F_6$ | | melting point: 54-56° C. |
| 191 | $H_3PO_3$ | $CX_3$ | 1 | $F_6$ | | melting point: 55-57° C. |
| 192 | $H_3PO_3$ | $CX_4$ | 1 | $F_6$ | | |
| 193 | $H_2SO_4$ | $CX_1$ | 2 | $F_6$ | | $n_D^{20}$: 1.4551 |
| 194 | $H_3PO_4$ | $CX_1$ | 2 | $F_6$ | | $n_D^{20}$: 1.4521 |
| 195 | $HClO_4$ | $CX_1$ | 3 | $F_6$ | | $n_D^{20}$: 1.4501 |
| 196 | $CH_3SO_4$ | $CX_1$ | 1 | $F_6$ | | $n_D^{20}$: 1.4512 |
| 197 | $H_3PO_3$ | $CX_3$ | 2 | $F_6$ | | |
| 198 | $HNO_3$ | $CX_1$ | 1 | $F_6$ | change on leaving to stand | $n_D^{20}$: 1.445 |
| 199 | $H_4SiO_4$ | $CX_1$ | 4 | $F_7$ | | $n_D^{20}$: 1.4530 |
| 200 | $H_4SiO_4$ | $CX_1$ | 2 | $F_7$ | | $n_D^{20}$: 1.4548 |
| 201 | "$SiO_2$" | $CX_1$ | 2 | $F_7$ | | $n_D^{20}$: 1.4563 |
| 202 | "$SiO_2$" | $CX_3$ | 2 | $F_7$ | | melting point: 63-65° C. |
| 203 | $H_3BO_3$ | $CX_3$ | 1 | $F_6$ | | melting point: 50-52° C. |
| 204 | $H_3BO_3$ | $C_{10}H_{21}O(CH_2C_2H_3O)_2H$ with OH | 2 | $F_6$ | | highly viscous liquid |

Explanation of the structure of the compound of the formula Z

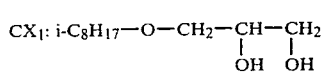

$CX_1$: i-$C_8H_{17}$—O—$CH_2$—CH—$CH_2$ with OH, OH

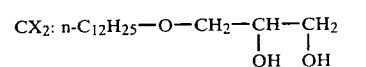

$CX_2$: n-$C_{12}H_{25}$—O—$CH_2$—CH—$CH_2$ with OH, OH

-continued

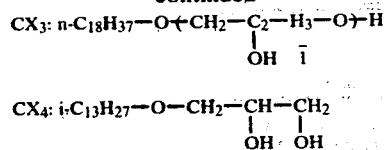

CX₄: i-C₁₃H₂₇—O—CH₂—CH—CH₂
                        |    |
                       OH   OH

EXAMPLE 205

Influence of the structure and the number of the chelating compounds on the solubility of the chelated metal salts in toluene and n-heptane The solubility characteristics of various chelated metal salts are summarised in Table 2. It can be seen from this that the products containing 1,2-propanediol as the ligand are insoluble. Products containing ethyl glycerol ether and i-propyl glycerol ether are somewhat soluble in toluene only when the number of ligands is high.

The compounds, according to the invention, containing n-pentyl glycerol ether and n-octyl glycerol ether as the chelating compounds of the formula Z (ligand) are already soluble in benzene when the number of ligands is low and with higher numbers of ligands are also soluble in n-heptane. In this respect a distinct improvement is observed in the transition from n-pentyl glycerol ether to n-octyl glycerol ether.

The influence of the structure of the chelating compounds (for the same number of ligands) of the formula Z can be seen from the following comparison:

The compound, according to the invention, $ZnCl_2$,

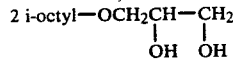

is soluble in toluene but not in n-heptane. If, for the same number of ligands, the i-octyl glycerol ether is replaced by i-tridecyl glycerol ether, this compound, according to the invention, is also soluble in n-heptane.

In Table 2 the symbols denote:
— slightly to very slightly soluble
+ readily soluble
++ very readily soluble

TABLE 2

| Ligand | Number of ligands | ZnCl₂ soluble in toluene | ZnCl₂ soluble in heptane | NiCl₂ soluble in toluene | NiCl₂ soluble in heptane | Cu(NO₃)₂ soluble in toluene | Cu(NO₃)₂ soluble in heptane | MgBr₂ soluble in toluene | MgBr₂ soluble in heptane |
|---|---|---|---|---|---|---|---|---|---|
| CH₃—CH—CH₂<br>    \|    \|<br>   OH   OH | 2 | — | — | — | — |  |  | — | — |
|  | 4 | — | — | — | — |  |  | — | — |
|  | 6 | — | — | — | — |  |  | — | — |
|  | 8 | — | — | — | — |  |  | — | — |
| C₂H₅—O—CH₂—CH—CH₂<br>              \|    \|<br>             OH   OH | 2 | — | — | — | — | — | — | — | — |
|  | 4 | — | — | — | — | — | — | — | — |
|  | 6 | — | — | — | — | — | — | — | — |
|  | 8 | — | — | — | — | — | — | — | — |
| *according to the invention* |  |  |  |  |  |  |  |  |  |
| i-C₃H₇—O—CH₂—CH—CH₂<br>              \|    \|<br>             OH   OH | 2 | + | — | + | — |  |  | + | — |
|  | 4 | + | + | + | + |  |  | + | + |
|  | 6 | ++ | + | ++ | + |  |  | ++ | + |
|  | 8 | ++ | + | ++ | + |  |  | ++ | + |
| n-C₅H₁₁—O—CH₂—CH—CH₂<br>                \|    \|<br>               OH   OH | 2 | + | + | +* | + | + | + | + | + |
|  | 4 | ++ | + | ++ | + | ++ | + | ++ | + |
|  | 6 | ++ | + | ++ | + | ++ | + | ++ | + |
|  | 8 | ++ | + | ++ | ++ | ++ | + | ++ | + |
| n-C₈H₁₇—O—CH₂—CH—CH₂<br>                \|    \|<br>               OH   OH | 2 | ++ | + | +* | +* | ++ | + | ++ | + |
|  | 4 | ++ | ++ | ++ | ++ | ++ | + | ++ | + |
|  | 6 | ++ | ++ | ++ | ++ | ++ | + | ++ | ++ |
|  | 8 | ++ | ++ | ++ | ++ | ++ | ++ | ++ | ++ |

*Products obtained in the crystalline form

EXAMPLE 206

Change in compounds according to the invention in air

The compounds listed in Table 3 are exposed to the influence of air for 15 days in open vessels. At the start, all the compounds, with the exception of two, were soluble in toluene and in n-heptane. The relatively high stability to air can be seen from the results in Table 3.

TABLE 3

Change in liquid metal salt chelates after standing in air for 15 days

| Compound according to the invention | Change | Solubility heptane | Solubility toluene | Remarks |
|---|---|---|---|---|
| MgF₂.4 i-C₈H₁₇—O—CH₂—CH—CH₂<br>                       \|    \|<br>                      OH   OH | substantial increase in viscosity | + | + |  |

TABLE 3-continued

Change in liquid metal salt chelates after standing in air for 15 days

| Compound according to the invention | Change | Solubility heptane | Solubility toluene | Remarks |
|---|---|---|---|---|
| $SnCl_4.4$ i-$C_8H_{17}$—O—$CH_2$—CH—$CH_2$ <br>                                     OH  OH | — | — | + | not completely soluble in n-heptane even at the start |
| $Ba_3(BO_3)_2.12$ i-$C_8H_{17}$—O—$CH_2$—CH—$CH_2$ <br>                                     OH  OH | formation of a skin | + | + | |
| $Cu(NO_3)_2.4$ i-$C_8H_{17}$—O—$CH_2$—CH—$CH_2$ <br>                                     OH  OH | — | + | + | |
| $Ni(HPO_3).4$ i-$C_8H_{17}$—O—$CH_2$—CH—$CH_2$ <br>                                     OH  OH | substantial increase in viscosity | + | + | |
| $BaCO_3.4$ i-$C_8H_{17}$—O—$CH_2$—CH—$CH_2$ <br>                                     OH  OH | solid separates out | + | + | |
| $CaS.4$ i-$C_8H_{17}$—O—$CH_2$—CH—$CH_2$ <br>                                     OH  OH | — | + | + | |
| $ZnCl_2.4$ i-$C_8H_{17}$—O—$CH_2$—CH—$CH_2$ <br>                                     OH  OH | — | + | + | |
| $Ba(HPO_4).4$ i-$C_8H_{17}$—O—$CH_2$—CH—$CH_2$ <br>                                     OH  OH | turbidity | + | + | turbidity does not go into solution |
| $Zn(HPO_4).4$ tert.$C_{12}H_{25}$—S—$CH_2$—CH—$CH_2$ <br>                                     OH  OH | turbidity | + | + | turbidity does not go into solution |
| $KI.4$ i-$C_8H_{17}$—O—($CH_2$—$C_2H_3$—O$)_{\overline{12}}$H <br>                                 OH | — | — | + | not completely soluble in n-heptane even at the start. |
| $Ba_2(SiO_4).8$ i-$C_8H_{17}$—O—$CH_2$—CH—$CH_2$ <br>                                     OH  OH | turbidity | + | + | turbidity does not go into solution |
| $BaSO_4.4$ i-$C_8H_{17}$—O—$CH_2$—CH—$CH_2$ <br>                                     OH  OH | — | + | + | |
| $SnBr_2.4$ i-$C_8H_{17}$—O—$CH_2$—CH—$CH_2$ <br>                                     OH  OH | — | + | + | |
| $LiOH.2$ i-$C_8H_{17}$—O—$CH_2$—CH—$CH_2$ <br>                                     OH  OH | turbidity | + | + | turbidity does not go into solution |
| $BF_3.2$ i-$C_{13}H_{27}$—O—$CH_2$—CH—$CH_2$ <br>                                     OH  OH | — | + | + | |

EXAMPLE 207

The values obtained by elementary analysis and the melting points of some compounds are given in Table 4. The figures in brackets indicate the theoretical values.

TABLE 4

Melting points and analytical data of crystalline compounds according to the invention

| Compound according to the invention | Recrystallised from | Melting point (°C.) | Analytical data O % | H % | Metal % | Halogen % | Good solubility at 23° C. heptane | toluene |
|---|---|---|---|---|---|---|---|---|
| $SnCl_4.2$ n-$C_{12}H_{25}$—O—$CH_2$—CH—$CH_2$ / OH  OH | heptane | 51–55 | 45.9 (46.1) | 8.2 (8.3) | 15.0 (15.2) | 17.7 (18.15) | | + |
| $NiCl_2.2$ n-$C_{12}H_{25}$—O—$CH_2$—CH—$CH_2$ / OH  OH | ethyl acetate/acetonitrile | 112–16 | 55.9 (55.4) | 9.9 (9.9) | 9.6 (9.0) | 10.3 (10.9) | | + |
| $FeCl_2.2$ n-$C_{12}H_{25}$—O—$CH_2$—CH—$CH_2$ / OH  OH | — | 59–64 | 53.7 (55.6) | 9.7 (10.0) | 8.6 (8.6) | 11.6 (10.95) | + | + |
| $ZnBr_2.3$ n-$C_{12}H_{25}$—O—$CH_2$—CH—$CH_2$ / OH  OH | acetonitrile | 48–50 | — | — | 6.5 (6.5) | 14.0 (15.9) | + | + |
| $MgCl_2.2$ n-$C_{12}H_{25}$—O—$CH_2$—CH—$CH_2$ / OH  OH | ethyl acetate | 99–101 | — | — | 3.8 (3.95) | 10.9 (11.5) | | + |
| $MgBr_2.2$ n-$C_{12}H_{25}$—O—$CH_2$—CH—$CH_2$ / OH  OH | ethyl acetate | 102–107 | — | — | 3.2 (3.45) | 21.6 (22.7) | | + |

EXAMPLE 208

The decomposition temperatures of some compounds according to the invention are indicated in Table 5; these temperatures were obtained by means of differential calorimetry. It is seen that the compounds have high stability to heat.

TABLE 5

| Compound according to the invention | Decomposition temperature (°C.) | Remarks |
|---|---|---|
| $CuSO_4.5$ i-$C_8H_{17}$—O—$CH_2$—CH—$CH_2.H_2O$ / OH  OH | >230 | loss of 1 mol of $H_2O$ above 110° C. |
| $BaSO_4.4$ i-$C_8H_{17}$—O—$CH_2$—CH—$CH_2$ / OH  OH | >230 | |
| $BaCO_3.4$ i-$C_8H_{17}$—O—$CH_2$—CH—$CH_2$ / OH  OH | >230 | |
| $NaBr.4$ i-$C_8H_{17}$—O—$CH_2$—CH—$CH_2$ / OH  OH | >230 | |
| $Cu[NO_3]_2.4$ i-$C_8H_{17}$—O—$CH_2$—CH—$CH_2$ / OH  OH | ~160 | |

EXAMPLE 209

Test to determine the stability to heat of complexed metal salts

Conditions:

A 30% strength solution in paraffin oil was heated at 220° C. in an oil bath for 3 minutes and any changes were then determined. The high stability to heat of the complexes according to the invention is seen in this case also.

| Substance | Change |
|---|---|
| $Mg[SO_3].3$ $CX_4$ | yellow coloration |
| $Ca[HPO_3].3$ $CX_4$ | — |
| $Ca[SO_3].3$ $CX_4$ | turbidity |
| $Ca[CNS]_2.3$ $CX_4$ | increase in viscosity |
| $Mg[H_2PO_2]_2.3$ $CX_4$ | turbidity (gel-like) |
| $Ca[H_2PO_2]_2.4$ $CX_4$ | — |
| $Mg[SiO_3].3$ $CX_4$ | — |
| $Ni[SiO_3].3$ $CX_4$ | — |
| $Ni[SiO_3].3$ $CX_3$ | slight turbidity |
| $Mg[HPO_3].3$ $CX_4$ | — |
| $Mn[H_2PO_3]_2.3$ $CX_3$ | — |
| $Ni[(HPO_3].3$ $CX_3$ | reversible phase separation above 200° C. |

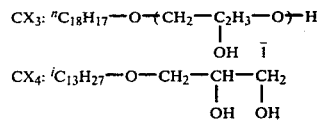

$CX_3$: n-$C_{18}H_{17}$—O—$(CH_2$—$C_2H_3$—O$)_{\overline{1}}$H / OH $CX_4$: i-$C_{13}H_{27}$—O—$CH_2$—CH—$CH_2$ / OH  OH

EXAMPLE 210

The activity of the compounds of the formula Z used according to the invention is determined by azeotropic dehydration of 0.05 mol of $AlCl_3.6H_2O$ in 100 ml of n-heptane in an apparatus with a water separator. The amount of water obtained after 8 hours is measured (theoretical amount 5.4 ml). The high reactivity of the glycerol monoethers and glycerol monothioethers can be seen from Table 6.

TABLE 6

| Chelating agent | Number | $H_2O$ driven out [ml] |
|---|---|---|
| i-$C_8H_{17}$—OH | 6 | 1.1 |

TABLE 6-continued

| Chelating agent | Number | H₂O driven out [ml] |
|---|---|---|
| n-$C_8H_{17}$—CH—CH₂<br>　　　　　｜　｜<br>　　　　　OH　OH | 4 | 1.1 |
| i-$C_8H_{17}$—O—CH₂—CH—CH₂<br>　　　　　　　　　｜　｜<br>　　　　　　　　　OH　OH | 4 | 4.4 |
| n-$C_6H_{13}$—S—CH₂—CH—CH₂<br>　　　　　　　　｜　｜<br>　　　　　　　　OH　OH | 4 | 5.2 |
| n-$C_6H_{13}$—SO—CH₂—CH—CH₂<br>　　　　　　　　　｜　｜<br>　　　　　　　　　OH　OH | 4 | 5.4* |

*after only 2 hours

EXAMPLE 211

The activity of the compounds of the formula Z used according to the invention is determined by the extent to which 0.05 mol of Ba(OH)₂.8H₂O is dissolved in 100 ml of n-heptane under the conditions of azeotropic dehydration. The activity is indicated by the residue of Ba(OH)₂ which has not dissolved, and is distinctly superior in the case of the glycerol ethers and glycerol thioethers, as can be seen from Table 7.

TABLE 7

| Chelating agent | Number | Residue as Ba(OH)₂ |
|---|---|---|
| i-$C_8H_{17}$—OH | 8 | 95% |
| n-$C_{12}H_{25}$—O—(CH₂—CH₂—O)ₙ₊₁—H | 4 | 81% |
| $C_3H_7$—CH—CH—CH₂—OH<br>　　　　｜　｜<br>　　　　OH　$C_2H_5$ | 4 | 60% |
| n-$C_6H_{13}$—S—CH₂—CH—CH₂<br>　　　　　　　　｜　｜<br>　　　　　　　　OH　OH | 4 | 0% |
| i-$C_8H_{17}$—O—CH₂—CH—CH₂<br>　　　　　　　　　｜　｜<br>　　　　　　　　　OH　OH | 4 | 0% |
| i-$C_8H_{17}$—O—CH₂—CH—CH₂<br>　　　　　　　　　｜　｜<br>　　　　　　　　　OH　OH | 2 | 20% |

II. USE EXAMPLE

EXAMPLE 212

Increase in the conductivity by the addition of compounds according to the invention to petroleum ether The resistance of a 0.1 percent strength by weight solution of one of the compounds according to the invention, mentioned in Table 8, in petroleum ether (boiling range 50°–70° C.) is determined at a terminal voltage of 1,000 V using the 1864 Megohmmeter of the General Radio Company and the specific conductivity is determined from this. Pure petroleum ether and i-octyl glycerol ether are also tested for purposes of comparison.

It is seen from Table 7 that the specific conductivity is increased by several powers of ten by the addition of even a small amount of compounds according to the invention and is superior to that of octyl glycerol monoether. The compounds according to the invention thus display an outstanding anti-static protective action.

TABLE 8

Conductivity of chelated metal salts in petroleum ether (50–70° C.) at a concentration of 0.1%

| Substance | Specific conductivity [Ω⁻¹ cm⁻¹] |
|---|---|
| Pure petroleum ether (50–70° C.) | $2.1 \times 10^{-16}$ |
| i-$C_8H_{17}$—O—CH₂—CH(OH)—CH₂OH | $1 \times 10^{-14}$ |
| ZnCl₂.4 i-$C_8H_{17}$—O—CH₂—CH(OH)—CH₂OH | $3.5 \times 10^{-13}$ |
| MgF₂.4 i-$C_8H_{17}$—O—CH₂—CH(OH)—CH₂OH | $2.1 \times 10^{-12}$ |
| Cu(NO₃)₂.4 i-$C_8H_{17}$—O—CH₂—CH(OH)—CH₂OH | $3.5 \times 10^{-12}$ |
| BaSO₄.4 i-$C_8H_{17}$—O—CH₂—CH(OH)—CH₂OH | $1 \times 10^{-10}$ |
| SnCl₄.4 i-$C_8H_{17}$—O—CH₂—CH(OH)—CH₂OH | $2.6 \times 10^{-12}$ |
| NiCl₂.4 i-$C_8H_{17}$—O—CH₂—CH(OH)—CH₂OH | $2.1 \times 10^{-10}$ |
| BF₃.2 i-$C_{13}H_{27}$—O—CH₂—CH(OH)—CH₂OH | $4.2 \times 10^{-10}$ |
| SnBr₂.4 i-$C_8H_{17}$—O—CH₂—CH(OH)—CH₂OH | $5.2 \times 10^{-12}$ |
| Ba₂SiO₄.8 i-$C_8H_{17}$—O—CH₂—CH(OH)—CH₂OH | $1.3 \times 10^{-11}$ |
| ZnSO₃.4 i-$C_8H_{17}$—O—CH₂—CH(OH)—CH₂OH | $2.1 \times 10^{-12}$ |
| CaCS₃.4 i-$C_8H_{17}$—O—CH₂—CH(OH)—CH₂OH | $3.5 \times 10^{-11}$ |
| BaCO₃.4 i-$C_8H_{17}$—O—CH₂—CH(OH)—CH₂OH | $2.1 \times 10^{-10}$ |
| Ba₃(BO₃)₂.12 i-$C_8H_{17}$—O—CH₂—CH(OH)—CH₂OH | $7 \times 10^{-12}$ |
| BaHPO₄.4 i-$C_8H_{17}$—O—CH₂—CH(OH)—CH₂OH | $1 \times 10^{-10}$ |
| NiHPO₃.4 i-$C_8H_{17}$—O—CH₂—CH(OH)—CH₂OH | $3.5 \times 10^{-12}$ |
| ZnHPO₄.4 tert.$C_{12}H_{25}$—S—CH₂—CH(OH)—CH₂OH | $1 \times 10^{-11}$ |
| Co(OAc)₂.4 tert.$C_{12}H_{25}$—S—CH₂—CH(OH)—CH₂OH | $2.1 \times 10^{-12}$ |

TABLE 8-continued

Conductivity of chelated metal salts in petroleum ether (50–70° C.) at a concentration of 0.1%

| Substance | Specific conductivity $[\Omega^{-1} \text{cm}^{-1}]$ |
|---|---|
| LiOH.2 i-C$_8$H$_{17}$—O—CH$_2$—CH(OH)—CH$_2$OH | $7 \times 10^{-12}$ |
| KI.4 i-C$_8$H$_{17}$—(CH$_2$—C$_2$H$_3$—O)$_{12}$H with OH | $2.1 \times 10^{-11}$ |
| H$_3$PO$_2$.i-C$_{13}$H$_{27}$—O—CH$_2$—CH(OH)—CH$_2$OH | $4 \times 10^{-9}$ |
| H$_2$SO$_4$.i-C$_8$H$_{17}$—O—CH$_2$—CH(OH)—CH$_2$OH | $5.1 \times 10^{-8}$ |
| H$_3$C—SO$_3$H.i-C$_8$H$_{17}$—O—CH$_2$—CH(OH)—CH$_2$OH | $2 \times 10^{-9}$ |
| H$_3$PO$_3$.n-C$_{18}$H$_{37}$—O—(CH$_2$—C$_2$H$_3$—O)$_{12}$H with OH | $7.4 \times 10^{-9}$ |

What is claimed is:

1. A complexed compound of the formula $$M_n^m . X_m^n . qZ$$

in which
M is a proton or a m-valent cation selected from the group consisting of Li$^+$, Na$^+$, K$^+$, Be$^{++}$, Mg$^{++}$, Ca$^{++}$, Ba$^{++}$, Al$^{+++}$, Ce$^{+++}$, Ti$^{+4}$, ZrO$^{++}$, Th$^{+4}$, Nb$^{+5}$, Cr$^{+++}$, Mo$^{+5}$, Mn$^{++}$, Fe$^{++}$, Fe$^{+++}$, Co$^{++}$, Ni$^{++}$, Cu$^{++}$, Ag$^+$, Zn$^{++}$, Cd$^{++}$, B$^{+++}$, Si$^{+4}$, Sn$^{++}$, Sn$^{+4}$, Pb$^{++}$, Sb$^{+++}$, Sb$^{+5}$, In$^{+++}$, Bi$^{+++}$, Hg$^{++}$ and Y$^{+3}$,
X is a n-valent anion selected from the group consisting of hydroxyl, fluoride, chloride, bromide, iodide, thiocyanate, perchlorate, sulfide, thiosulfate, sulfate, acetate, nitrate, hydrogen phosphite, borate, carbonate, sulfite, silicate, hydrogen phosphate, titanate, phosphate, metadisilicate, metasilicate, metatrisilicate, hypophosphinite, metatitanate, methoxy, dihydrogen phosphite, metaborate, zirconate, oxide, metaphosphite, phosphite, trithiocarbonate, methylsulfonate, trifluoromethylsulfonate, octoxycarbonylmethylmercaptide, 2-(octoxycarbonyl)ethylmercaptide and β-carboxyethylmercaptide;
m is an integer from 1 to 5,
n is an integer from 1 to 4,
Z is a chelate-forming compound of the formula $$R^3—L—(CH_2CHOHCH_2O)_x—H$$

where
R$^3$ is alkyl of 3 to 18 carbon atoms,

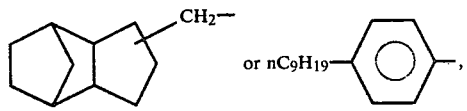

L is O or S,
x is an integer from 1 to 3, and
q is an integer from 1 to 12.

2. A complexed compound of the formula $$M_n^m . X_m^n . qZ$$

in which
M is a proton or a m-valent cation selected from the group consisting of Li$^+$, Na$^+$, K$^+$, Mg$^{++}$, Ca$^{++}$, Ba$^{++}$, Fe$^{++}$, Fe$^{+++}$, Co$^{++}$, Ni$^{++}$, Cu$^{++}$, Zn$^{++}$, B$^{+++}$, Sn$^{++}$ and Sn$^{+4}$,
X is a n-valent anion selected from the group consisting of hydroxyl, fluoride, chloride, bromide, iodide, sulfate, acetate, nitrate, hydrogen phosphite, borate, carbonate, sulfite, silicate, hydrogen phosphate, phosphate, hypophosphinite, dihydrogen phosphite, phosphite, trithiocarbonate and methylsulfonate,
m is an integer from 1 to 4,
n is an integer from 1 to 4,
Z is a chelate-forming compound of the formula $$R^3—L—(CH_2CHOHCH_2O)_x—H$$

where
R$^3$ is alkyl of 8 to 18 carbon atoms,
L is O or S,
x is an integer from 1 to 2, and
q is an integer from 1 to 12.

3. A compound according to claim 1, of the composition I, which corresponds to the formula $$H_3PO_3.2C_{18}H_{37}—O(CH_2—C_2H_3O)_1—H \text{ with } OH$$

4. A compound according to claim 1, of the composition I, which corresponds to the formula $$H_4SiO_4.2C_{18}H_{37}—O(CH_2—C_2H_3O)_1—H \text{ with } OH.$$

5. A compound according to claim 1, of the composition I, which corresponds to the formula $$BaSO_4.4i—C_8H_{17}—O—CH_2—CHOH—CH_2OH.$$

6. A compound according to claim 1, of the composition I, which corresponds to the formula $$BF_3.2i—C_{13}H_{27}—OCH_2—CHOH—CH_2OH.$$

* * * * *